United States Patent
Knox

(10) Patent No.: US 9,029,569 B2
(45) Date of Patent: May 12, 2015

(54) USE OF ALPHA-HYDROXY CARBONYL COMPOUNDS AS REDUCING AGENTS

(75) Inventor: Richard J. Knox, Carmarthen (GB)

(73) Assignee: Morvus Technology Limited, Carmarthen (GB)

( * ) Notice: Subject to any disclaimer, the term of this patent is extended or adjusted under 35 U.S.C. 154(b) by 1290 days.

(21) Appl. No.: 12/159,363

(22) PCT Filed: Dec. 29, 2006

(86) PCT No.: PCT/GB2006/004947
§ 371 (c)(1),
(2), (4) Date: Dec. 30, 2008

(87) PCT Pub. No.: WO2007/074344
PCT Pub. Date: Jul. 5, 2007

(65) Prior Publication Data
US 2010/0104515 A1    Apr. 29, 2010

(30) Foreign Application Priority Data
Dec. 29, 2005   (GB) .................................. 0526552.5

(51) Int. Cl.
| | | |
|---|---|---|
| C07D 203/14 | (2006.01) | |
| C07B 31/00 | (2006.01) | |
| A61K 31/04 | (2006.01) | |
| A61K 31/045 | (2006.01) | |
| A61K 31/12 | (2006.01) | |
| A61K 31/396 | (2006.01) | |
| A61K 45/06 | (2006.01) | |

(52) U.S. Cl.
CPC .............. *A61K 31/04* (2013.01); *C07D 203/14* (2013.01); *C07B 31/00* (2013.01); *A61K 31/045* (2013.01); *A61K 31/12* (2013.01); *A61K 31/396* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,208,999 A | | 9/1965 | Jarowenko at al. |
| 3,658,788 A | * | 4/1972 | Orgel et al. ................ 536/27.11 |
| 4,154,747 A | | 5/1979 | Epple et al. |
| 4,251,536 A | | 2/1981 | Johnson |
| 4,375,394 A | * | 3/1983 | Devon ........................... 205/450 |
| 4,950,306 A | | 8/1990 | Marte et al. |
| 5,633,158 A | | 5/1997 | Anlezark et al. |
| 5,780,585 A | | 7/1998 | Anlezark et al. |
| 5,831,097 A | | 11/1998 | Ebel et al. |
| 5,873,912 A | | 2/1999 | Carlough |
| 5,977,065 A | | 11/1999 | Anlezark et al. |
| 2003/0086933 A1 | * | 5/2003 | Burke et al. ............... 424/181.1 |
| 2003/0228285 A1 | | 12/2003 | Hung et al. |
| 2004/0044055 A1 | | 3/2004 | Lieb et al. |
| 2004/0053208 A1 | | 3/2004 | Zavizion et al. |

FOREIGN PATENT DOCUMENTS

| | | |
|---|---|---|
| DE | 41 03 639 A1 | 8/1992 |
| EP | 0 330 432 A1 | 8/1989 |
| EP | 0 364 752 A2 | 4/1990 |
| EP | 0 540 263 A1 | 5/1993 |
| GB | 2 035 803 A | 6/1980 |
| GB | 2 365 338 A | 2/2002 |
| JP | 52-145523 A | 12/1977 |
| WO | WO-88/07378 A1 | 10/1988 |
| WO | WO-89/07592 A1 | 8/1989 |
| WO | WO-93/08288 A1 | 4/1993 |
| WO | WO-95/35100 A1 | 12/1995 |
| WO | WO-96/03151 A2 | 2/1996 |
| WO | WO-96/03151 A3 | 2/1996 |
| WO | WO-97/23456 A1 | 7/1997 |
| WO | WO-98/35701 A1 | 8/1998 |
| WO | WO-98/52547 A1 | 11/1998 |
| WO | WO-98/57662 A2 | 12/1998 |
| WO | WO-98/57662 A3 | 12/1998 |
| WO | WO-99/32113 A1 | 7/1999 |
| WO | WO-99/61409 A1 | 12/1999 |
| WO | WO-00/10611 A2 | 3/2000 |
| WO | WO-00/10611 A3 | 3/2000 |
| WO | WO-01/64739 A1 | 9/2001 |
| WO | WO-02/30909 A1 | 4/2002 |
| WO | WO-2004/035769 A1 | 4/2004 |
| WO | WO-2004/110536 A1 | 12/2004 |
| WO | WO-2005/002570 A1 | 1/2005 |
| WO | WO-2005/080002 A1 | 9/2005 |
| WO | WO-2006/003492 A2 | 1/2006 |
| WO | WO-2006/003492 A3 | 1/2006 |
| WO | WO-2007/026166 A2 | 3/2007 |
| WO | WO-2007/026166 A3 | 3/2007 |

OTHER PUBLICATIONS

"Spectrophotometric Determination of Reducing Sugars with Aromatic Nitro Compounds" by Soloniewicz et al., Mikrochim. Acta I, 105-14 (1982).*

"Method for selection of solvents for promotion of organic reactions" by Gani et al., Computers Chem. Eng. 29, 1661-76 (2005).*

"Acids and Bases" in March's Advanced Organic Chemistry, 5th Ed., by Smith et al., John Wiley & Sons, Inc. (New York), pp. 327-362 (2001).*

Definition of "alkaline" from A Dictionary of Chemistry, 3rd Ed., by Daintith, Oxford University Press (New York), p. 19 (1996).*

(Continued)

*Primary Examiner* — Theodore R West
(74) *Attorney, Agent, or Firm* — Morrison & Foerster LLP

(57) ABSTRACT

There is provided the use as reducing agents of alpha-hydroxycarbonyl compounds capable of forming cyclic dimers. There is also provided corresponding methods of reducing reducible compounds, particularly reduction-activated prodrugs. Examples of the alpha-hydroxycarbonyl compounds used are dihydroxyacetone, glycolaldehyde, glyceraldehyde, erythrose, xylulose, erythrulose or 3-hydroxy-2-butanone.

10 Claims, 7 Drawing Sheets

(56) References Cited

OTHER PUBLICATIONS

Definition of "alkaline" from McGraw-Hill Dictionary of Chemical Terms by Parker, McGraw-Hill Book Co. (New York), p. 15 (1984).*
Definition of "alkali" from Hawley's Condensed Chemical Dictionary, 13th Ed., by Lewis, John Wiley & Sons, Inc. (New York), p. 33 (1997).*
Helsby, N.A. et al. (2004). "2-Amino Metabolites are Key Mediators of CB 1954 and SN 23862 Bystander Effects in Nitroreductase GDEPT," *British Journal of Cancer* 90:1084-1092.
Sunters, A. et al. (1991). "Cytotoxicity and Activation of CB1954 in a Human Tumour Cell Line," *Biochemical Pharmacology* 41(9):1293-1298.
Tang, M.H.Y. et al. (2005, e-published Aug. 29, 2005). "Aerobic 2- and 4-Nitroreduction of CB 1954 by Human Liver," *Toxicology* 216:129-139.
Tisdale, M.J. et al. (1980). "Selective Inhibition of Ribonucleotide Reductase by the Monofunctional Alkylating Agent 5(1-Aziridinyl)-2,4-Dinitrobenzamide (CB 1954)," *Biochemical Pharmacology* 29:2845-2853.
Workman, P. et al. (Aug. 1984). "Pharmacology of the Mixed-Function Radio- and Chemosensitizers CB 1954 and RSU 1069," *International Journal of Radiation Oncology Biology Physics* 10(8):1307-1310.
Partial European Search Report mailed Feb. 16, 2011, for EP Patent Application No. 10075381.3, filed Dec. 29, 2006, 5 pages.
Choudry, G.A. et al. (2001). "A Novel Strategy for NQO1 (NAD(P)H:Quinone Oxidoreductase, EC 1.6.99.2) Mediated Therapy of Bladder Cancer Based on the Pharmacological Properties of EO9," *British Journal of Cancer* 85(8):1137-1146.
Adams, G.E. et al. (Mar. 1980). "Toxicity of Nitro Compounds Toward Hypoxic Mammalian Cell in Vitro: Dependence on Reduction Potential," *JNCI* 64(3):555-560.
Aghi, M. et al. (2000). "Prodrug Activation Enzymes in Cancer Gene Therapy," *The Journal of Gene Medicine* 2:148-164.
Angyal, S.J. et al. (1980). "The Composition of Reducing Segars in Aqueous Solution: Glyceraldehyde, Erythrose, Threose," *Aust. J. Chem.* 33:1001-1011.
Chen, S. et al. (1995). "Catalytic Properties of NAD(P)H:Quinone Acceptor Oxidoreductase: Study Involving Mouse, Rat, Human, and Mouse-Rat Chimeric Enzymes," *Molecular Pharmacology* 47:934-939.
Chen, S. et al. (Jan. 17, 1997). "Molecular Basis of the Catalytic Differences Among DT-Diaphorase of Human, Rat, and Mouse," *The Journal of Biological Chemistry* 272(3):1437-1439.
Chung-Faye, G. et al. (Sep. 2001). "Virus-Directed, Enzyme Prodrug Therapy with Nitroimidazole Reductase: A Phase I and Pharmacokinetic Study of its Prodrug, CB1954," *Clinical Cancer Research* 7:2662-2668.
Cobb, L.M. et al. (1969). "2,4-Dinitro-5-Ethyleneiminobenzamide (CB 1954): A Potent and Selective Inhibitor of the Growth of the Walker Carcinoma 256," *Biochemical Pharmacology* 18:1519-1527.
Cobb, L.M. (1970). "Toxicity of the Selective Antitumor Agent 5-Aziridino-2,4-Dinitrobenzamide in the Rat," *Toxicology and Applied Pharmacology* 17:231-238.
Collins, J.M. et al. (Aug. 1999). "Suicide Prodrugs Activated by Thymidylate Synthase: Rationale for Treatment and Noninvasive Imaging of Tumors with Deoxyuridine Analogues," *Clinical Cancer Research* 5:1976-1981.
Connors, T.A. et al. (1971). "Studies on the Mechanism of Action of 5-Aziridinyl-2,4-Dinitrobenzamide (CB 1954), A Selective Inhibitor of the Walker Tumour," *Int. J. Cancer* 7:86-92.
Croft, S.L. et al. (1999). "Animal Models of Visceral Leishmaniasis," Chapter 94 in *Handbook of Animal Models of Infection*, pp. 1-3.
Cui, W. et al. (1999). "Nitroreductase-Mediated Cell Ablation is Very Rapid and Mediated by a p53-Independent Apoptotic Pathway," *Gene Therapy* 6:764-770.
Cui, W. et al. (2001). "Inducible Ablation of Astrocytes Shows That These Cells are Required for Neuronal Survival in the Adult Brain," *GLIA* 34:272-282.

Ernster, L. (1987). "DT Diaphorase: A Historical Review," *Chemica Scripta* 27A:1-13.
Felmer, R. (2002). "Inducible Ablation of Adipocytes in Adult Transgenic Mice Expressing the *E. coli* Nitroreductase Gene," *Journal of Endocrinology* 175:487-498.
Friedlos, F. et al. (1992). "The Properties of Total Adducts and Interstrand Crosslinks in the DNA of Cells Treated with CB 1954, Exceptional Frequency and Stability of the Crosslink," *Biochemical Pharmacology* 43(6):1249-1254.
Friedlos, F. et al. (1998). "Gene-Directed Enzyme Prodrug Therapy: Quantitative Bystander Cytotoxicity and DNA Damage Induced by CB1954 in Cells Expressing Bacterial Nitroreductase," *Gene Therapy* 5:105-112.
Glushonok, G.K. et al. (2003). "A 1H and 13C NMR and UV Study of the State of Hydroxyacetone in Aqueous Solutions," *Russian Journal of General Chemistry* 73(7):1027-1031.
Gutierrez, P.L. (Jul. 1, 2000). "The Metabolism of Quinone-Containing Alkylating Agents: Free Radical Production and Measurement," *Frontiers in Bioscience* 5:d629-d638.
Hauge, J.G. et al. (1955). "Oxidation of Dihydroxyacetone via the Pentose Cycle in Acetobacter Suboxydans," *J. Biol. Chem.* 214:11-26.
Heller, J. et al. (1968). "Reduction by Non-Sugar Compounds Occurring in Biological Material," *Bulletin de L'Academie Polonaise des Sciences* 16(7):401-405.
Hu, L. et al. (2003). "Nitroaryl Phosphoramides as Novel Prodrugs for *E. coli* Nitroreductase Activation in Enzyme Prodrug Therapy," *Journal of Medicinal Chemistry* 46(23):4818-4821.
Huang, M-T. et al. (Nov. 25, 1979). "Rat Liver Cytosolic Azoreductase," *The Journal of Biological Chemistry* 254(22):11223-11227.
Ilg, H. et al. (1965). CAPLUS Accesion No. 1966:68533. "Possible Applications of Reductonates in the Fixation of Vat Dyes by the Two-Stage Printing Process," *Textil-Praxis* 20(11):916-920. (English Abstract Only).
Isles, A.R. et al. (2001). "Conditional Ablation of Neurones in Transgenic Mice," *J. Neurobiol.* 47:183-193.
Kammerer, C. et al. (2004). "Synergistic Effect of Dehydroascorbic Acid and Mixtures with Vitamin E and β-Carotene on Mitomycin C Efficiency Under Irradiation In Vitro," *In Vivo* 18:795-798.
Khan, A.H. et al. (1969/70). "Tumour-Growth Inhibitory Nitrophenylaziridines and Related Compounds: Structure-Activity Relationships," *Chem.-Biol. Interactions* 1:27-47.
Knox, R.J. et al. (Apr. 1986). "Mechanism of Cytotoxicity of Anticancer Platinum Drugs: Evidence that cis-Diamminedichloroplatinum(II) and cis-Diammine-(1,1-Cyclobutanedicarboxylato)platinum(II) Differ Only in the Kinetics of Their Interaction with DNA," *Cancer Research* 46:1972-1979.
Knox, R.J. et al. (1987). "The Effect of Monofunctional or Difunctional Platinum Adducts and of Various Other Associated DNA Damage on the Expression of Transfected DNA in Mammalian Cell Lines Sensitive or Resistant to Difunctional Agents," *Biochimica et Biophysica Acta* 908:214-223.
Knox, R.J. et al. (1988). "A New Cytotoxic, DNA Interstrand Crosslinking Agent, 5-(Aziridin-1-YL)-4-Hydroxylamino-2-Nitrobenzamide, is Formed from 5-(Aziridin-1-YL)-2,4-Dinitrobenzamide (CB 1954) by a Nitroreductase Enzyme in Walker Carcinoma Cells," *Biochemical Pharmacology* 37(24):4661-4669.
Knox, R.J. et al. (1988). "The Nitroreductase Enzyme in Walker Cells that Activates 5-(Aziridin-1-YL)-2,4-Dinitrobenzamide (CB 1954) to 5-(Aziridin-1-YL)-4-Hydroxylamino-2-Nitrobenzamide is a Form of NAD(P)H Dehydrogenase (Quinone) (EC 1.6.99.2)," *Biochemical Pharmacology* 37(24):4671-4677.
Knox, R.J. et al. (1991). "Bioactivation of CB 1954: Reaction of the Active 4-Hydroxylamino Derivative with Thioesters to Form the Ultimate DNA-DNA Interstrand Crosslinking Species," *Biochemical Pharmacology* 42(9):1691-1697.
Knox, R.J. et al. (1991). "The Walker 256 Carcinoma: A Cell Type Inherently Sensitive Only to Those Difunctional Agents that can Form DNA Interstrand Crosslinks," *Mutation Research, DNA Repair* 225:227-240.
Knox, R.J. et al. (1992). "The Bioactivation of 5-(Aziridin-1-YL)-2,4-Dinitrobenzamide (CB1954)—II, A Comparison of an

(56) References Cited

OTHER PUBLICATIONS

*Escherichia coli* Nitroreductase and Walker DT Diaphorase," *Biochemical Pharmacology* 44(12):2297-2301.
Knox, R.J. et al. (1993). "Identification, Synthesis and Properties of 5-(Aziridin-1-YL)-2-Nitro-4-Nitrosobenzamide, A Novel DNA Crosslinking Agent Derived From CB1954," *Biochemical Pharmacology* 46(5):797-803.
Knox, R.J. et al. (1993). "The Bioactivation of CB 1954 and its Use as a Prodrug in Antibody-Directed Enzyme Prodrug Therapy (ADEPT)," *Cancer and Metastasis Reviews* 12:195-212.
Knox, R.J. et al. (Aug. 1, 2000). "Bioactivation of 5-(Aziridin-1-YL)-2,4-Dinitrobenzamide (CB1954) by Human NAD(P)H Quinone Oxidoreductase 2: A Novel Co-Substrate-Medicated Antitumor Prodrug Therapy," *Cancer Research* 60:4179-4186.
Knox, R.J. et al. (2003). "CB 1954: From the Walker Tumor to NQO2 and VDEPT," *Current Pharmaceutical Designs* 9(26) :2091-2104.
Knox, R.J. et al. (2004). "Quinone Reductase-Mediated Nitro-Reduction: Clinical Applications," *Methods in Enzymology* 382:194-221.
Li, Z. at al. (2003). "Nitrobenzocyclophosphamides as Potential Prodrugs for Bioreductive Activation: Synthesis, Stability, Enzymatic Reduction, and Antiproliferative Activity in Cell Culture," *Bioorganic & Medicinal Chemistry* 11:4171-4178.
Loadman, P.M. et al. (2000). "Pharmacological Properties of a New Aziridinylbenzoquinone, RH1 (2,5-Diaziridiny1-3-(Hydroxymethyl)-6-Methyl-1,4-Benzoquinone), in Mice," *Biochemical Pharmacology* 59:831-837.
Ma, D. et al. (2002). "Selective Ablation of Olfactory Receptor Neurons Without Functional Impairment of Vomeronasal Receptor Neurons in OMP-ntr Transgenic Mice," *European Journal of Neuroscience* 16:2317-2323.
Malisza, K.L. et al. (Feb. 1, 1995). "Doxorubicin Reduces the Iron(III) Complexes of the Hydrolysis Products of the Antioxidant Cardioprotective Agent Dexrazoxane (ICRF-187) and Produces Hydroxyl Radicals," *Archives of Biochemistry and Biophysics* 316(2):680-688.
Mauger, A.B. et al. (1994). "Self-lmmolative Prodrugs: Candidates for Antibody-Directed Enzyme Prodrug Therapy in Conjunction with a Nitroreductase Enzyme," *Journal of Medicinal Chemistry* 37(21):3452-3458.
Murray, H.W. et al. (Jul. 1993). "Treatment of Experimental Visceral Leishmaniasis in a T-Cell-Deficient Host: Response to Amphotericin B and Pentamidine," *Antimicrobial Agents and Chemotherapy* 37(7):1504-1505.
Nelson, N. (1944). "A Photometric Adaptation of the Somogyi Method for the Determination of Glucose," *The Journal of Biological Chemistry* 153:375-380.
Neumüller, A.O. (1981). "Glycerol Aldehyde," Römpps Chemie-Lexikon 8*th* Edition, p. 1513. (English translation).
Post, J. et al. (Jul. 1, 1963). "The Replication Time and Pattern of the Liver Cell in the Growing Rat," *The Journal of Cell Biology* 18:1-12.
Pozas, R. et al. (2005). "Synthesis and in vitro Antitrypanosomal Activity of Novel Nifurtimox Analogues," *Bioorganic & Medicinal Chemistry Letters* 15:1417-1421.
Prochaska, H.J. et al. (Jan. 25, 1986). "Purification and Characterization of Two Isofunctional Forms of NAD(P)H:Quinone Reductase from Mouse Liver," *The Journal of Biological Chemistry* 261(3):1372-1378.
Rauth, A.M. et al. (1998). "Bioreductive Therapies: An Overview of Drugs and Their Mechanisms of Action," *Int. J. Radiation Oncology Biol. Phys.* 42(4):755-762.
Ross, W.C.J. et al. (1969). "A Spectrophotometric Method for the Estimation of the Carcinostatic Agent, 5-Aziridino-2,4-Dinitrobenzamide (CB 1954), in Biological Fluids," *Biochemical Pharmacology* 18:2683-2688.
Sheard, C.E. et al. (1971). "The Sensitivity to Chemotherapeutic Agents of a Rat Tumour Grown in Immunosuppressed Mice," *Br. J. Cancer* 25:838-844.

Skelly, J.V. et al. (2001). "Aerobic Nitroreduction by Flavoproteins: Enzyme Structure, Mechanisms and Role in Cancer Chemotherapy," *Mini Revies in Medicinal Chemistry* 1(3):1-14.
Smyth, T.P. et al. (1998). "S-Aminosulfeniminopenicillins: Multimode β-Lactamase Inhibitors and Template Structures for Penicillin-Based β-Lactamase Substrates as Prodrugs," *J. Org. Chem.* 63(22):7600-7618.
Venitt, S. et al. (1987). "The Toxicity and Mutagenicity of the Anti-Tumour Drug 5-Aziridino-2,4-Dinitrobenzamide (CB1954) is Greatly Reduced in a Nitroreductase-Deficient Strain of *E. coli*," *Mutagenesis* 2(5):375-381.
Von Ardenne, M. (1964). CAPLUS Accesion No. 1967:17926. "Calculation of the Effective Dosage of Glyceraldehyde in the Tissue on Application in the Circulation," *Naturwissenschaften* 51:217-218. (English Abstract Only).
Weedon, S.J. et al. (2000). "Sensitisation of Human Carcinoma Cells to the Prodrug CB1954 by Adenovirus Vector-Mediated Expression of *E. coli* Nitroreductase," *Int. J. Cancer* 86:848-854.
Wei, Y. et al. (2000). "Activation of Antibacterial Prodrugs by Peptide Deformylase," *Bioorganic & Medicinal Chemistry Letters* 10:1073-1076.
Woessner, R. et al. (2000). "Comparison of Three Approaches to Doxorubicin Therapy: Free Doxorubicin, Liposomal Doxorubicin, and β-Glucuronidase-Activated Prodrug (HMR 1826)," *Anticancer Research* 20:2289-2296.
Wolkenberg, S.E. (2001). "In situ Activation of Antitumor Agents," *Tetrachedron Letters* pp. 1-5.
Workman, P. et al (1986). "CB 1954 Revisited—I. Disposition Kinetics and Metabolism," *Cancer Chemother. Pharmacol.* 16:1-8.
Workman, P. et al. (1986). "CB 1954 Revisited—II. Toxicity and Antitumour Activity," *Cancer Chemother. Pharmacol.* 16:9-14.
Wright, J.D. (Date Unknown). "Bioreductive Agents and Their Role in Chemotherapy," in PhD Thesis for Univ. of Essex pp. 13-28.
Wu, K. et al. (Nov. 15, 1997). "Catalytic Properites of NAD(P)H:Quinone Oxidoreductase-2 (NQO2), a Dihydronicotinamide Riboside Dependent Oxidoreductase," *Archives of Biochemistry and Biophysics* 347(2):221-228.
Wu, K. et al. (Jan. 1, 2001). "Demonstration of the Activation of Prodrug Cb 1954 Using Human DT-Diaphorase Mutant Q104Y-Transfected MDA-MB-231 Cells and Mouse Xenograft Model," *Archives of Biochemistry and Biophysics* 385(1):203-208.
Anlezark, G.M. et al. (1992). "The Bioactivation of 5-(Aziridin-1-YL)-2,4-Dinitrobenzamide (CB1954)—I, Purification of Properties of a Nitroreductase Enzyme from *Escherichia coli*—A Potential Enzyme for Antibody-Directed Enzyme Prodrug Therapy (ADEPT)," *Biochemical Pharmacology* 44(12):2289-2295.
Anlezark, G.M. et al. (1995). "Bioactivation of Dinitrobenzamide Mustards by an *E. coli* B Nitroreductase," *Biochemical Pharmacology* 50(5):609-618.
Anonymous. (2005). "International Nonproprietary Names for Pharmaceutical Substances (INN)," *WHO Drug Information* 19(2):161-198.
Apple, M.A. et al. (Dec. 1968). "Arrest of Cancer in Mice by Therapy with Normal Metabolites. II. Indefinite Survivors Among Mice Treated with Mixtures of 2-Oxopropanal (NSC-79019) and 2,3-Dihydroxypropanal (NSC-67934)," *Cancer Chemotherapy Reports (Part 1)* 52(7):687-696.
Bailey, S.M. et al. (1996). "Investigation of Alternative Prodrugs for Use with *E. coli* Nitroreductase in 'Suicide Gene' Approaches to Cancer Therapy," *Gene Therapy* 3:1143-1150.
Boland, M.P. et al. (1991). "The Differences in Kinetics of Rat and Human DT Diaphorase Result in a Differential Sensitivity of Derived Cell Lines to CB 1954 (5-(Aziridin-1-YL)-2,4-Dinitrobenzamide)," *Biochemical Pharmacology* 41(6/7):867-875.
Bridgewater, J.A. et al. (1995). "Expression of the Bacterial Nitroreductase Enzyme in Mammalian Cells Renders Them Selectively Sensitive to Killing by the Prodrug CB1954," *European Journal of Cancer* 31A(13/14):2362-2370.
Bridgewater, J.A. et al. (Apr. 10, 1997). "The Bystander Effect of the Nitroreductase/CB1954 Enzyme/Prodrug System is Due to a Cell-Permeable Metabolite," *Human Gene Therapy* 8:709-717.

(56) References Cited

OTHER PUBLICATIONS

Buckner, F.S. et al. (Nov. 1996). "Efficient Technique for Screening Drugs for Activity Against *Trypanosoma cruzi* Using Parasites Expressing β-Galactosidase," *Antimicrobial Agents and Chemotherapy* 40(11):2592-2597.

Anonymous. (2013). "Reduction of Tretazicar by Various α-Hydroxy Carbonyl Compounds," one page.

Morvus Technology Ltd. (2013). "Morvus Technology Inc.: Synthesis of MTL004," two pages.

Perlin, A.S. et al. (1955). "A New Method for the Preparation of D-Erythrose and of L-Glyceraldehyde," *Can. J. Chem.* 33:1216-1221.

Lewis, R.C. et al. (1915). "A Method for the Estimation of Sugar in Small Quantities of Blood," *J. Biol. Chem.* 20:61-72.

Milroy, J.A. (1925). "CXIV. A Method for the Estimation of Glucose in Blood," *Biochem. J.* 19:746-749.

Momose, T. et al. (1964). "Organic Analysis. XLIX. Color Reaction of 3,4-, 4,5-, or 3,5-Dinitrophthalic Acid with Reducing Sugars," *Chem. Pharm. Bull.* 12(1):14-18.

Soloniewicz, R. et al. (1977). "New Colour Reaction for the Determination of Reducing Sugars," *Z. Anal. Chem.* 283:304 (with English Machine Translation).

Soloniewicz, R. et al. (1978). "Determination of Reducing Sugars with Nitro Derivative of Anthraquinone," *Chemia Analityczna* 23:645-652 (with English Abstract Only).

Sumner, J.B. et al. (1921). "Dinitrosalicylic Acid: A Reagent for the Estimation of Sugar in Normal and Diabetic Urine," *J. Biol. Chem.* 47:5-9.

Teodorczyk, M. et al. (1977). "Colorimetric Determination of Reducing Sugars Using o-Nitrobenzoic Acid," *Chemia Analityczna* 22:151-154 (with English Abstract Only).

\* cited by examiner $C_9H_8N_4O_5$
252.18
C 42.9%; H 3.2%; N 22.2%; O 31.7%

USE OF ALPHA-HYDROXY CARBONYL COMPOUNDS AS REDUCING AGENTS

CROSS-REFERENCE TO RELATED APPLICATIONS

This application is a National Phase application under 35 U.S.C. §371 of International Application No. PCT/GB2006/004947 filed Dec. 29, 2006 and claims the benefit of Great Britain Application No. 0526552.5 filed Dec. 29, 2005, the disclosures of which are incorporated herein by reference in their entirety.

The present invention relates to the use of certain compounds as reducing agents. In particular, it relates to the use of those compounds to reduce a reduction-activated prodrug, which produces active substances that may be used in combating disease. The active substance may, in particular, be a DNA cross-linking agent, which can be employed to combat undesirable cell growth or proliferation.

The listing or discussion of a prior-published document in this specification should not necessarily be taken as an acknowledgement that the document is part of the state of the art or is common general knowledge.

α-Hydroxy carbonyl compounds, although molecules that are capable of being oxidised, are not recognised to be useful as reducing agents under conditions of low alkalinity (pH<11).

Certain α-hydroxy carbonyl compounds (acyloins) are mentioned in U.S. Pat. No. 5,831,097 and EP 0 364 752 as being useful as reducing agents in the dyeing industry. However, the conditions specified in EP 0 364 752 require a minimum pH of 13 for the achievement of the reducing effect. Similarly, U.S. Pat. No. 4,950,306 discloses that certain compounds (including α-hydroxy carbonyl compounds) can be used as reducing agents in a dyeing process, but only if sufficient alkali is added to the reaction medium to establish a pH of at least 11.

Further, although other documents (e.g. U.S. Pat. No. 3,208,999 and *Textil-Praxis* 20(11), 916-20 (1965)) mention the use of certain α-hydroxy carbonyl compounds (e.g. monohydroxyacetone and dihydroxyacetone) as being useful as reducing agents for certain compounds (cyanoethylated starches and vat dyes), the reaction conditions mentioned in these documents are highly alkaline (i.e. requiring the use of significant quantities of concentrated solutions of either ammonium or sodium hydroxide, resulting in reaction pH values of over 13).

In addition, none of the above-mentioned documents discloses (in relation to reductions utilising α-hydroxy carbonyl compounds) the use of solvent systems comprising more than 10% by weight of an organic solvent.

The inventor has now unexpectedly discovered that certain α-hydroxy carbonyl compounds do possess useful reducing ability at relatively low pH values, and can therefore be employed under mild conditions (and/or in the presence of substantial quantities of non-aqueous (organic) solvents) to reduce various moieties, including a wide range of organic compounds.

Thus, a first aspect of the invention provides the use of a compound of formula I as an agent for reducing a reducible group in an organic compound containing one or more such groups, wherein the compound of formula I has the structure

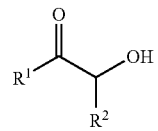

wherein
R¹ represents H, aryl, Het or $C_{1-12}$ alkyl, which latter group is optionally substituted by one or more substituents selected from OH, halo and $C_{1-3}$ alkoxy,
R² represents H or $C_{1-6}$ alkyl, which latter group is optionally substituted by one or more OH groups,
aryl represents a $C_{6-10}$ carbocyclic aromatic group, which group may be substituted by one or more substituents selected from halo, $C_{1-6}$ alkyl and $C_{1-6}$ alkoxy,
Het represents a 4- to 14-membered heterocyclic group containing one or more heteroatoms selected from oxygen, nitrogen and/or sulfur, which heterocyclic group may comprise one, two or three rings and may be substituted by one or more substituents selected from halo, $C_{1-6}$ alkyl and $C_{1-6}$ alkoxy,
which compound is characterised in that it is capable of forming a cyclic dimer of formula Ia

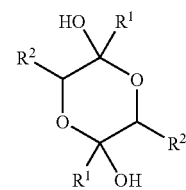

wherein R¹ and R² are as hereinbefore defined.

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Examples of aryl groups that may be mentioned include phenyl, naphthyl and the like.

Heterocyclic (Het) groups may be fully saturated, partly unsaturated, wholly aromatic or partly aromatic in character. Values of heterocyclic (Het) groups that may be mentioned include 1-azabicyclo[2.2.2]octanyl, benzimidazolyl, benzo [c]isoxazolidinyl, benzisoxazolyl, benzodioxanyl, benzodioxepanyl, benzodioxolyl, benzofuranyl, benzofurazanyl, benzomorpholinyl, 2,1,3-benzoxadiazolyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]furanyl, 1,3-dihydrobenzo-[c]furanyl, 1,3-dihydro-2,1-benzisoxazolyl 2,3-dihydropyrrolo[2,3-b]pyridinyl, dioxanyl, furanyl, hexahydropyrimidinyl, hydantoinyl, imidazolyl, imidazo[1,2-α]pyridinyl, imidazo[2,3-b]thiazolyl, indolyl, isoquinolinyl, isoxazolidinyl, isoxazolyl, maleimido, morpholinyl, naphtho[1,2-b]furanyl, oxadiazolyl, 1,2- or 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3 -b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo [e]pyrimidine, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl, xanthenyl and the like.

Substituents on heterocyclic (Het) groups may, where appropriate, be located on any atom in the ring system including a heteroatom. The point of attachment of heterocyclic (Het) groups may be via any atom in the ring system including (where appropriate) a heteroatom, or an atom on any fused carbocyclic ring that may be present as part of the ring system.

The term "halo", when used herein, includes fluoro, chloro, bromo and iodo.

Compounds of formula I that may be mentioned (in relation to all aspects of the invention) include those in which:
(1) $R^1$ is other than H;
(2) $R^1$ represents H or, particularly, $C_{1-2}$ alkyl substituted by one or more OH groups (e.g. $CH_2OH$);
(3) $R^2$ represents $C_{1-4}$ alkyl substituted by one or more OH groups (e.g. $CH_2OH$ or $CH(OH)CH_2OH$) or, particularly, H.

Further, specific compounds of formula I that may be mentioned (in relation to all aspects of the invention) include dihydroxyacetone (DHA, alternatively named as 1,3-dihydroxy-2-propanone), glycolaldehyde, glyceraldehyde, erythrose, xylulose, and dimers thereof. Other specific compounds of formula I that may be mentioned include erythrulose and 3-hydroxy-2-butanone. In one particular embodiment of the invention (all aspects thereof), the compound of formula I is DHA or a dimer thereof.

For the avoidance of doubt, because the compounds of formula I can exist in both dimeric and monomeric forms, references herein to compounds of formula I include references to those compounds in either form (unless the context indicates otherwise). Further, the ability of compounds of formula I to exist in the form of a cyclic dimer of formula Ia is inherent to the structure of those compounds. Thus, references herein to generically or specifically defined compounds of formula I, all of which compounds are capable of forming a cyclic dimer of formula Ia, includes references to those (generically or specifically defined) compounds as such (i.e. without the above-described characterising feature relating to the formation of a cyclic dimer). Whether or not a compound of formula I is capable of forming a cyclic dimer of formula Ia may be determined, for example, by studying the propensity of the isolated compound to form said cyclic dimer in either the solid or solution (e.g. aqueous solution or organic solution) state.

An alternative aspect of the invention provides the use of a compound of formula I, as hereinbefore defined, as an agent for reducing a reducible inorganic compound.

In one embodiment of this aspect of the invention, the inorganic compound is not iodine or does not comprise cupric ions or ferricyanide.

The inorganic compound may, in particular embodiments, comprise a lanthanide (e.g. cerium) or, particularly, a transition metal (i.e. a metal of group IIIA to IIB). The inorganic compound may comprise a coordination complex of said lanthanide or transition metal. Particular transition metals that may be mentioned include those in the cobalt and nickel groups (i.e. metals having $d^9$ or $d^{10}$ electronic configurations in the neutral state), such as cobalt or platinum. The metal may (in a coordination complex or otherwise) be in an oxidation state that is higher than another, stable oxidation state for that metal. For example; for cobalt the III oxidation state may be reduced to the II oxidation state; for platinum, the IV oxidation state may be reduced to the II oxidation state. In certain embodiments of this aspect of the invention, the transition metal is other than iron or copper.

In a particular embodiment of the first aspect of the invention, the use of the compound of formula I as an agent for reducing a reducible group in an organic compound comprises the use of such a compound as a reducing agent for a compound other than an enzyme.

In another embodiment of the first aspect of the invention, the reduction of the reducible compound takes place in a non-aqueous solvent system. When used herein, the term "non-aqueous solvent system" includes references to chlorinated hydrocarbons (such as dichloromethane), hydrocarbons (e.g. hexane), aromatic hydrocarbons (e.g. toluene or xylene), dipolar aprotic solvents (e.g. N,N-dimethylformamide, N,N-dimethylacetamide, dimethylsulfoxide or N-methylpyrrolidinone), acetonitrile, esters (e.g. ethyl acetate) or, particularly, lower ($C_{1-4}$) alkyl alcohols (such as isopropanol, ethanol or methanol). The term "non-aqueous solvent system" also includes references to mixtures of such solvents.

It has been found that reduction by compounds of formula I can be promoted by the addition of base. Thus, a particular embodiment of the first aspect of the invention relates to the use of a compound of formula I, as hereinbefore defined, and base for reducing a reducible group in an organic compound containing one or more such groups.

In this embodiment, the base may be organic or inorganic. For example, the base may be an amine (e.g. a primary, secondary or, particularly, tertiary amine, such as triethylamine, trimethylamine or diethylisopropylamine), a nitrogen-based heterocycle (e.g. N-methylmorpholine or pyridine), an alkoxide (e.g. an alkali metal alkoxide, such as sodium ethoxide), a hydroxide salt (e.g. an ammonium or alkali metal hydroxide, such as sodium or potassium hydroxide) or, particularly, a carbonate or bicarbonate salt (e.g. an alkaline earth or, particularly, an alkali metal carbonate or bicarbonate).

The amount of base employed can vary, depending upon factors such as the particular compound of formula I selected, the identity of compound to be reduced, the rate of reaction that is desired, etc. However, in certain embodiments of the first aspect of the invention, the amount of base employed may be, for example, four (e.g. three, two or one) or fewer equivalents relative to the compound of formula I, such as a catalytic quantity of base (e.g. 0.1 equivalents or less). N,N-dimethylformamide. Alternatively, the base may provide the reaction mixture with a certain pH level. Thus, in other embodiments of the first aspect of the invention, the compound of formula I is used as a reducing agent that effects reduction at a pH (e.g. in aqueous solution) of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)).

When used herein, the term "aqueous solution" refers to solutions of substances in which the solvent system comprises water, and optionally further comprises one or more other solvents, such as water-miscible organic solvents (e.g. a lower (such as $C_{1-4}$) alkyl alcohol, such as ethanol, isopropanol or, particularly, methanol). Further, when pH values are referred to herein, those values may be determined by methods known to those skilled in the art (e.g. by potentiometric measurements using a working and a reference electrode), for example at room temperature (such as 25° C.).

The compound of formula I may also be employed in a method of reducing a reducible compound. Thus, according to a second aspect of the invention, there is provided a method of reducing a reducible group in an organic compound, said method comprising contacting said compound with a compound of formula I, as hereinbefore defined.

In a particular embodiment of the second aspect of the invention, the method is for reducing a compound other than an enzyme.

In another embodiment of the second aspect of the invention, the method comprises contacting the reducible compound with a compound of formula I in the presence of a non-aqueous solvent system, as hereinbefore defined. In a particular embodiment, the reduction takes place in said non-aqueous solvent system.

In another particular embodiment of the second aspect of the invention, the method is carried out in the presence of base, such as a base as defined in respect of the first aspect of the invention. The amount of base employed may be, for example, one or fewer equivalents relative to the compound of formula I, such as a catalytic quantity of base (e.g. 0.1 equivalents or less)

In another particular embodiment of the second aspect of the invention, the method comprises contacting the reducible compound with a compound of formula I, as hereinbefore defined, in the presence of a solution (e.g. an aqueous solution) or suspension having a pH of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)). Alternatively, the method comprises contacting the reducible compound with a compound of formula I, as hereinbefore defined, in the presence of a solution or suspension (in a certain volume of a substantially non-aqueous solvent system, as defined below) of an amount of base that, if dissolved or suspended in the equivalent volume of water, would produce a pH of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)).

In the first and second aspects of the invention, the group that is reduced may be, for example, a nitro, an oxo (e.g. a keto, such as a quinone carbonyl), an imino, an azo, an N-oxide or pyridinium group. In particular, that is reduced may be, for example a nitro or pyridinium group.

As mentioned hereinbefore, it has been surprisingly discovered that reductions utilising α-hydroxy carbonyl compounds can be performed in the presence of substantial quantities of (or exclusively in) non-aqueous (organic) solvents.

Thus, an alternative aspect of the invention relates to the use of a compound of formula I, as hereinbefore defined, as a reducing agent in a substantially non-aqueous solvent system.

When used herein, the term "substantially non-aqueous solvent system" includes references to solvent systems comprising at most 80% (e.g. 70, 60, 50, 40, 30, 20, 10, 5, 1 or 0.1%) by weight of water. In these solvent systems, the remainder of solvent (i.e. the at least 20% by weight) is an organic solvent. Organic solvents that may be mentioned in this respect include those mentioned above in relation to the term "non-aqueous solvent system". The term "substantially non-aqueous solvent system" also includes references to wholly non-aqueous solvent systems (e.g. solvent systems comprising exclusively organic solvents).

As before, a particular embodiment of this aspect of the invention relates to the use of a compound of formula I, as hereinbefore defined, and base as a reducing agent in substantially non-aqueous solvent systems.

In this aspect of the invention, the compound of formula I may be used to reduce either an organic or an inorganic compound (e.g. an organic compound as described below).

The invention further provides a corresponding method of reduction utilising a compound of formula I and substantially non-aqueous solvent systems. Thus, a further aspect of the invention relates to a method of reducing a reducible compound, said method comprising contacting said reducible compound with a compound of formula I, as hereinbefore defined, and a substantially non-aqueous solvent system.

In a particular embodiment of this aspect of the invention the method comprises contacting the reducible compound with a compound of formula I, as hereinbefore defined, and base.

Also in this aspect of the invention, the reducible compound may be either an organic or an inorganic compound (e.g. an organic compound as described below).

When, in this aspect of the invention, the reducible compound is an inorganic compound, the inorganic compound may, in particular embodiments:
(i) not be iodine or not comprise cupric ions or ferricyanide;
(ii) comprise a lanthanide (e.g. cerium) or, particularly, a transition metal (i.e. a metal of group IIIA to IIB); and/or
(iii) comprise a coordination complex of said lanthanide or transition metal.

Particular transition metals that may be mentioned include those in the cobalt and nickel groups (i.e. metals having $d^9$ or $d^{10}$ electronic configurations in the neutral state), such as cobalt or platinum. The metal may (in a coordination complex or otherwise) be in an oxidation state that is higher than another, stable oxidation state for that metal. For example; for cobalt the III oxidation state may be reduced to the II oxidation state; for platinum, the IV oxidation state may be reduced to the II oxidation state. In certain embodiments of this aspect of the invention, the transition metal is other than iron or copper.

The product of the reduction may be a biologically active substance. Thus, third and fourth aspects of the invention provide, respectively:
(i) the use of a compound of formula I, as hereinbefore defined, as an activating agent for the conversion of a reduction-activated prodrug to a corresponding active substance; and
(i) a method of reducing a reduction-activated prodrug, the method comprising contacting the reduction-activated prodrug with a compound of formula I, as hereinbefore defined.

A particular embodiment of the third aspect of the invention relates to the use as an activating agent for the conversion of a reduction-activated prodrug to a corresponding active substance of a compound of formula I, as hereinbefore defined, and base. The identity and quantity of the base employed, as well as the pH at which the compound of formula I effects activation (by reduction) of the prodrug, may be as defined in respect of the use of the first aspect of the invention.

Correspondingly, in a particular embodiment of the fourth aspect of the invention, the method is carried out in the presence of base, such as a base as defined in respect of the first aspect of the invention. The identity and quantity of the base employed may be as defined in respect of the use of the first aspect of the invention. Further, in another particular embodiment of the fourth aspect of the invention, the method comprises contacting the reduction-activated prodrug with a compound of formula I, as hereinbefore defined, in the presence of a solution (e.g. an aqueous solution) or suspension having a pH of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)). Alternatively, the method comprises contacting the reduction-activated prodrug with a compound of formula I, as hereinbefore defined, in the presence of a solution or suspension (in a certain volume of a substantially non-aqueous solvent system, as hereinbefore defined) of an amount of base that, if dissolved or suspended in an equivalent volume of water, would produce a pH of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)).

The term "prodrug" will be well understood by those skilled in the art. For the avoidance of doubt, however, the term "reduction-activated prodrug" is used herein to include references to compounds that may or may not possess pharmacological activity as such, but that can be converted, by a process involving a reduction step, to a substance (i.e. a "corresponding active substance") having pharmacological activity, or at least appreciably greater pharmacological activity than the "prodrug" moiety.

When used herein, the term "activating agent" includes references to the compounds of formula I acting, by a reduction process, to convert, or to initiate the conversion of, the prodrug into a corresponding biologically active substance.

Reduction-activated prodrugs that may be mentioned in this respect (and in relation to all relevant aspects of the invention) include:

(a) Metronidazole (2-methyl-5-nitro-1H-imidazole-1-ethanol);
(b) Chloramphenicol (2,2-dichloro-N-[(αR,βR)-β-hydroxy-α-hydroxymethyl-4-nitrophenethyl]acetamide);
(c) Nitrofurazone (2-[(5-nitro-2-furanyl)methylene]hydrazinecarboxamide);

Metronidazole, Chloramphenicol and Nitrofurazone are cytotoxic to mammalian cells if activated (Bailey et al (1996)).

(d) EO9 (3-[5-aziridinyl-4,7-dioxo-3-hydroxymethyl-1-methyl-1H-indol-2-yl]-prop-β-ene-α-ol);
(e) SR-4233 ("tirapazamine", 3-amino-1,2,4-benzotriazine-1,4-dioxide);
(f) RSU-1069 (1-(1-aziridinyl)-3-(2-nitro-1-imidazolyl)-2-propanol);
(g) RB-6145 (1-[3-(2-bromoethylamino)-2-hydroxypropyl]-2-nitroimidazole);
(h) AQ4N (1,4-bis([2-(dimethylamino-N-oxide)ethyl]amino)5,8-dihydroxy-anthracene-9,10-dione);
(i) RB90003X

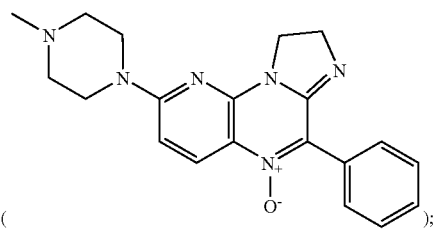 [SMILES: CN1CCN(c2ccc3c(n2)N2CCN=C2C(c2ccccc2)=[N+]3[O-])CC1]

(j) Mitomycin C;
(k) Mitosene;
(l) Cyclopropamitosene;
(m) Dynemycin A;
(n) a compound of the formula

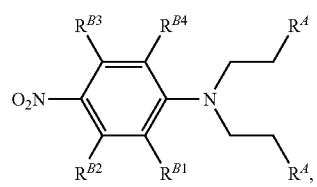

wherein
each $R^A$ independently represents chloro, bromo, iodo or —OS(O)$_2R^C$,
$R^C$ represents $C_{1-8}$ alkyl (optionally substituted by one or more fluoro atoms) or phenyl (optionally substituted by one or more substituents selected from halo, nitro, $C_{1-4}$ alkyl and $C_{1-4}$ alkoxy),
$R^{B1}$ to $R^{B4}$ independently represent H, CN, C(O)N($R^D$)$R^E$, C(S)N($R^D$)$R^E$, C(O)OH, S(O)$_2$NHR$^F$,
or $R^{B1}$ may additionally represent NO$_2$,
$R^D$ and $R^E$ independently represent H or $C_{1-4}$ alkyl (which latter group is optionally substituted by one or more substituents selected from OH, N(H)—$C_{1-2}$ alkyl, N($C_{1-2}$ alkyl)$_2$, 4-morpholinyl and C(O)OH),
or $R^D$ and $R^E$, together with the N-atom to which they are attached, represent 4-morpholinyl, and
$R^F$ represents H or S(O)$_2$CH$_3$,
provided that $R^{B2}$ is H when $R^{B1}$ is other than H,
for example, any one of the compounds of the above formula disclosed in Anlezark et al., 1992 and 1995, such as SN 23163, SN 23849, SN 23777, SN 23428, SN 23759, SN 24927, SN 24928, SN 24926, SN 25402, SN 25079, SN 24939, SN 24935, SN 25923, SN 25313, SN 23856, SN 25066, SN 23816, SN 25015, SN 24971, SN 25260, SN 25261, SN 25263, SN 25084, SN 25188, SN 25507 or, particularly, SN 23862 (5-{N,N-bis[2-chloroethyl]amine}-2,4-dinitrobenzamide);

(o) a compound of the formula

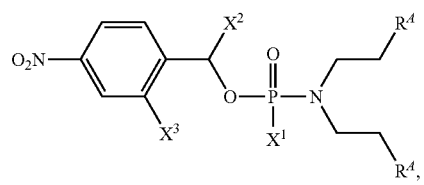

wherein
$R^A$ is as defined above (e.g. Cl) and either
$X^1$ represents NH$_2$ and $X^2$ and $X^3$ both represent H,
—$X^1$—$X^2$— represents —NH—CH$_2$CH$_2$— and $X^3$ represents H or
—$X^1$—$X^3$— represents —NH— and $X^2$ represents H;

(p) a compound of the formula

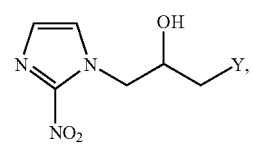

wherein Y represents
1-aziridinyl (optionally substituted at the 2-position by methyl), methoxy (thus forming the compound misonidazole) or N(H)CH$_2$CH$_2$Br (thus forming the compound RB6145);

(q) a self-immolative prodrug of the formula

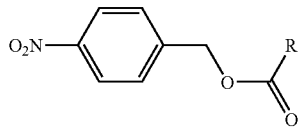

wherein
R represents —O—R' or —NH—R',
R' represents

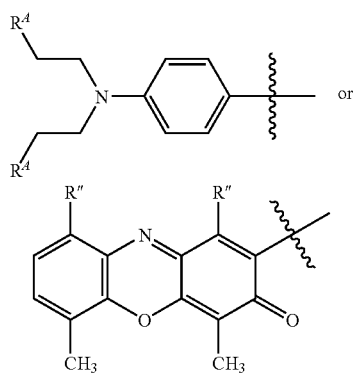

in which the wavy line indicates the position of attachment of the fragments,
R$^A$ is as defined above (e.g. Cl) and
R" represents the following peptide lactone

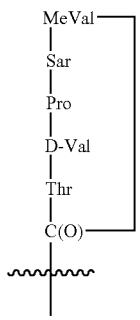

in which the wavy line indicates the position of attachment of the fragment,
for example compounds of the above formula in which R represents —NH—R', or in which R represents —O—R' and R' represents

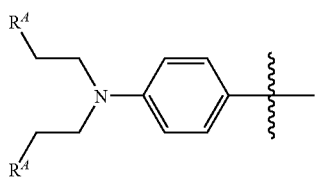

in which R$^A$ is as defined above (e.g. Cl);

Self-immolative prodrugs are described in Hu et al, 2003; Li et al, 2003 and Manger et al, 1994.

(r) a nitroindoline compound of the formula

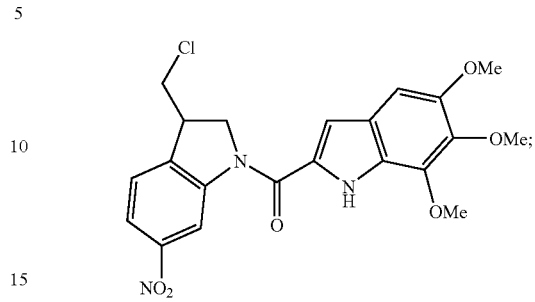

(s) acridine-CB 1954

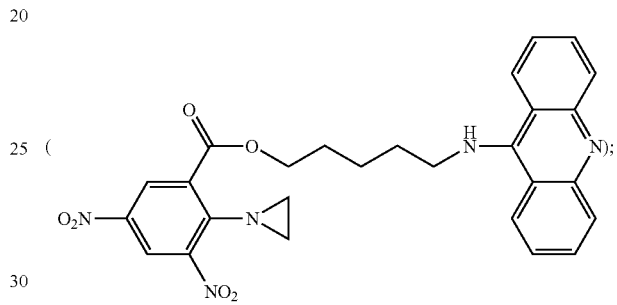

(t) tretazicar (5-(aziridin-1-yl)-2,4-dinitrobenzamide);
(u) a benzoquinone, naphthoquinone or anthraquinone for use in anti-cancer chemotherapy or disease treatment, where potency is dependent upon reduction of the quinone function, such as
a 2,5-bis(1-aziridinyl)-1,4-benzoquinone of the formula

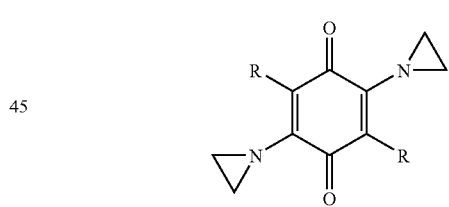

wherein each R independently represents H or NR'C(O)OR" and wherein R' represents H or C$_{1-4}$ alkyl and R" represents C$_{1-4}$ alkyl (e.g. each R represents NHC(O)OC$_2$H$_5$, thus forming diaziquone ("AZQ"), or each R represents H, thus forming 2,5-bis(1-aziridinyl)-1,4-benzoquinone ("DZQ")),
benzoquinone mustard (2-(N,N-bis[2-chloroethyl]amino)-1,4-benzoquinone),
adriamycin or
a mitomycin;
(v) conjugate prodrugs containing a quinonoid residue that release a cytotoxic agent upon reductive activation (for example as described in WO 99/61409, the disclosures of which document are hereby incorporated by reference), such as a compound of the formula

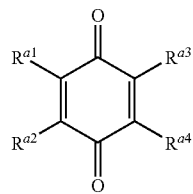

wherein $R^{a1}$ represents methyl, $N(C_{1-2}$ alkyl$)_2$ or, together with $R^{a2}$ represents a fused pyrrole or furan ring (which ring is optionally substituted by one or more substituents selected from methyl and hydroxymethyl), $R^{a2}$ represents methyl or, together with $R^{a1}$ represents a fused pyrrole or furan ring (which ring is optionally substituted by one or more substituents selected from methyl and hydroxymethyl), $R^{a3}$ represents a structural fragment of the formula

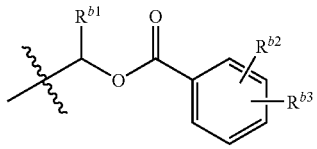

wherein the wavy line represents the point of attachment of the fragment, $R^{b1}$ represents H or methyl, $R^{b2}$ represents $N(CH_2CH_2Cl)_2$ (e.g. in the 3- or 4-position) and $R^{b3}$ represents methyl (e.g. at the 4-position) or $OR^{c1}$ (e.g. at the 3-position, wherein $R^{c1}$ represents $C_{1-6}$ alkyl (such as n-butyl) or $C_{3-6}$ cycloalkylmethyl (such as cyclopropylmethyl or cyclobutylmethyl);

(w) a reducible benzoquinone, naphthoquinone, anthraquinone or indoloquinone used as a non-cytotoxic platform for prodrug conjugates where the quinone acts as a trigger component for drug release (for example as described in WO 97/23456 or WO 98/35701, the disclosures of which documents are hereby incorporated by reference), such as a compound of the formula

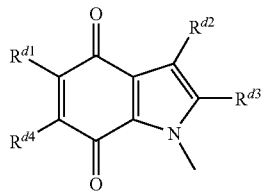

wherein $R^{d1}$ represents $C_{1-4}$ alkoxy, aziridin-1-yl (optionally substituted by one or two methyl groups), —N(H)CH$_2$C(CH$_3$)$_2$OH or a structural fragment of the formula

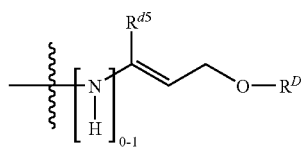

wherein the wavy line represents the point of attachment of the fragment, $R^{d5}$ represents H or methyl and $R^D$ represents a drug moiety, $R^{d2}$ represents methyl, —C(O)O(C$_{1-4}$alkyl) or —OCH$_2$OR$^{e1}$, $R^{e1}$ represents a drug moiety, H, $R^{e2}$—C(O)OR$^{e3}$ or —C(O)NH$_2$, $R^{e2}$ and $R^{e3}$ independently represent phenyl, benzyl or cyclohexyl, which latter three groups are optionally substituted by one or more substituents selected from halo, nitro, acyloxy and —SH $R^{d3}$ represents $C_{1-3}$ alkyl optionally substituted by OH (e.g. methyl, isopropyl or 2-hydroxyethyl) or $C_{3-6}$ cycloalkyl (e.g. cyclopropyl or cyclohexyl), $R^{d4}$ represents H, $C_{1-4}$ alkyl, $N(R^{e4})R^{e5}$ or $N(R^{e6})C(O)OR^{e7}$, $R^{e4}$ to $R^{e6}$ independently represent H or $C_{1-4}$ alkyl and $R^{e7}$ represents $C_{1-4}$ alkyl, or a compound of the formula

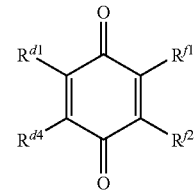

wherein $R^{f1}$ and $R^{f2}$ independently represent H, $C_{1-4}$ alkyl or $R^{f1}$ and $R^{f2}$ together represent a fused benzene ring (which ring is optionally substituted by one or more substituents selected from methyl and methoxy) and $R^{d1}$ and $R^{d4}$ are as defined above; and (w) a nitroaromatic or nitroheterocyclic compound for use as a prodrug trigger platform through "self alkylation" after reductive activation in a drug-releasing system (for example as described in WO 00/10611, the disclosures of which document are hereby incorporated by reference), such as a compound of the formula

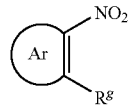

wherein Ar represents an aromatic (e.g. phenyl, naphthyl or anthracenyl) ring or a heteroaromatic (e.g. pyrrolyl, imidazolyl, (benzo)furanyl, (benzo)thienyl, (benz)oxazolyl, (benzo)thiazolyl, pyridinyl, pyrimidinyl, pyrazinyl, indolyl or (iso)quinolinyl) ring, which ring is optionally substituted by one or more substituents selected from $C_{1-4}$ alkyl, $C_{1-4}$ alkoxy, OH, halo, $N(R^{e4})R^{e5}$ and $C(O)OR^{e6}$ (wherein $R^{e4}$ to $R^{e6}$ are as defined above), R^g represents a structural fragment of the formula

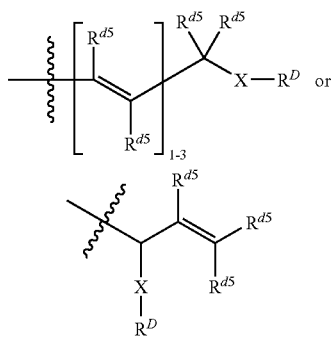

wherein the wavy line represents the point of attachment of the fragment and each $R^{d5}$ and $R^D$ is, independently at each occurrence, as defined above,
or a pharmaceutically acceptable salt and/or solvate thereof (e.g. a compound as defined at (a) to (t) above).

In this aspect of the invention, embodiments that may be mentioned include those wherein the reduction-activated prodrug is converted to the corresponding active substance by reduction of a nitro group.

Indeed, in a particular embodiment, the compounds of formula I are used to activate the prodrug tretazicar (5-(aziridin-1-yl)-2,4-dinitrobenzamide; also known as CB1954; see FIG. 1 for its structure).

Tretazicar is an example of an agent that can be used to combat proliferative disorders. There are many disorders in which it is desirable to prevent or reduce cell growth or proliferation. Some of these diseases, such as cancer, are life-threatening and others, although not life-threatening, are debilitating (such as psoriasis) or irritating and uncomfortable (such as warts). One strategy of combating these diseases, notably cancer, is to make use of chemical agents which are able to effect the cross-linking of DNA and which prevent or reduce cell growth or proliferation. Tretazicar achieves this cross-linking, but only after it has been reduced (at a nitro group) to the corresponding hydroxylamine (which is then further activated as discussed below).

Tretazicar has been the subject of continuing interest for over 35 years. It was first synthesised in the late 1960s as part of a series of potential anti-cancer compounds that had been studied since the early 1950s. When synthesised and tested, tretazicar appeared to represent the vision of cancer chemotherapy—a small, low molecular weight compound that could cure tumours with minimal toxic side-effects. As an anti-cancer agent, it represents one of the very few examples of a compound that shows a real anti-tumour selectivity. Unfortunately, for the treatment of human cancer, this anti-tumour selectivity was seen only in certain rat tumours. The basis for the anti-tumour selectivity of tretazicar is that it is a prodrug that is enzymatically activated to generate a difunctional agent, which can form DNA-DNA interstrand crosslinks. The bioactivation of tretazicar in rat cells involves the aerobic reduction of its 4-nitro group to a 4-hydroxylamine by the enzyme NQO1 (DT-diaphorase) (FIG. 2). The human form of NQO1 metabolises tretazicar much less efficiently than rat NQO1. Thus human cells and tumours are insensitive to tretazicar.

There is an additional endogenous tretazicar-reducing enzyme in human tumour cells and its activity is much greater than that attributable to NQO1 (Knox et al, 2000) (Wu et al, 1997). However, this activity is latent and only detectable in the presence of dihydronicotinamide riboside (NRH) (Knox et al, 2000) and not in the presence of either NADH or NADPH. The enzyme responsible for this activity is human NAD(P)H quinone oxidoreductase2 (NQO2) (Knox et al, 2000) (Wu et al, 1997). In the presence of NRH, NQO2 can catalyse the two-electron reduction of quinones and the four-electron nitroreduction of tretazicar (Wu et al, 1997). NQO2 can be considered as a human NRH-dependent nitroreductase.

5-(Aziridin-1-yl)-4-hydroxylamino-2-nitrobenzamide is highly cytotoxic, even to those cells resistant to tretazicar and can form interstrand crosslinks in their DNA. It is the formation of this compound that accounts for the sensitivity of cells when they are able to activate tretazicar. Irrespective of the ability to bioactivate tretazicar, all the cell types appear have a comparable sensitivity towards the reduced 4-hydroxylamino derivative (Boland et al, 1991). While 5-(aziridin-1-yl)-4-hydroxylamino-2-nitrobenzamide can produce DNA-DNA interstrand crosslinks in cells, it cannot form these lesions in naked DNA (Knox et al, 1991a). There is a further activation step that converts 5-(aziridin-1-yl)-4-hydroxylamino-2-nitrobenzamide to the proximal, DNA crosslinking, cytotoxic species. An enzymatic esterification and activation of the hydroxylamine, analogous to that formed by metabolism of 4-nitroquinoline-N-oxide and N-acetylaminofluorene, was proposed (Knox et al, 1991a). In fact, 5-(aziridin-1-yl)-4-hydroxylamino-2-nitrobenzamide can be activated non-enzymatically, to a form capable of reacting with naked DNA to produce interstrand crosslinks, by a direct chemical reaction with acetyl-coenzyme A and other thioesters (Knox et al, 1991a) (FIG. 2). The ultimate, DNA-reactive, derivative of tretazicar is probably 4-(N-acetoxy)-5-(aziridin-1-yl)-2-nitrobenzamide.

The bioactivation of tretazicar results in a vast increase in its cytotoxicity and the resulting dose modification can be up to 100,000 fold. This is greater than would be predicted even by conversion of a mono- to a difunctional agent. Where monofunctional congeners of difunctional agents are available, as with half mustards and monofunctional platinum compounds, the dose modification for equitoxicity is seen to be only around 50-200 fold (Knox et al, 1991b; Knox et al, 1987). However, observations regarding the formation of DNA interstrand crosslinks and their properties explain why there is such a large increase in the cytotoxicity of tretazicar following its activation.

(i). The tretazicar induced interstrand crosslink is formed with a very high frequency and can contribute up to 70% of the total lesions (Friedlos et al, 1992). This frequency is much higher than that reported for most other agents. For example, interstrand crosslinks represent 2% or less of the total DNA reactions of Cisplatin or Carboplatin (Knox et al, 1986). The interstrand crosslink is, in terms of molar efficacy, a more intrinsically toxic lesion than single-strand di-adducts and monofunctional lesions. An agent that produced a very high proportion of crosslinks would be expected to be more toxic than one that produced only a low frequency.

(ii). The crosslinks are poorly repaired which may be cause them to be even more intrinsically cytotoxic than those induced by other difunctional agents (Friedlos et al, 1992).

(iii). As a consequence of the bioactivation of the tretazicar, there is a 10-fold increase in the amount of DNA-bound drug in Walker cells, as compared to cells which cannot reduce tretazicar (Friedlos et al, 1992).

These unusual properties of the tretazicar-induced interstrand crosslink suggest that it is not like those formed by other agents. The interstrand crosslink lesion(s) induced by tretazicar has yet to be fully identified. However, the 4-hydroxylamine, (after activation as detailed above) reacts predominantly with the C8 position of deoxyguanosine. In DNA, this would leave the aziridine function poised to react on the opposing strand and form the observed crosslinks. Molecular modelling studies indicate that this second arm reaction will preferentially be on the O6 position of a deoxyguanosine on the opposite strand of DNA (Knox et al, 2003; Knox et al, 1991a). Such a C8-O6 DNA interstrand crosslink would be unique as it is not produced by other types of alkylating or platinating agents, and may account for unique properties of tretazicar.

These properties, coupled with the selectivity of the bioactivation step, explain why tretazicar was so exceptionally effective as an anti-tumour agent in the rat and provides the rationale for its use in G(V)DEPT and activation by NQO2 in humans (Knox et al, 2003) (Burke & Knox, 1998).

Tretazicar can also be used for selective cell ablation in transgenic animals. Conditional targeted ablation of specific cell populations in living transgenic animals is a very powerful strategy to determine cell functions in vivo. Targeted ablation is achieved by constructing a transgene incorporating a bacterial nitroreductase that can activate tretazicar aerobically (NTR) (Anlezark et al, 1992; Knox et al, 1992) and appropriate tissue specific promoters and injecting this into the fertilised eggs of the animal under study—normally mice. After birth, genomic integration of the transgene is confirmed and founder mice bred to establish the transgenic lines. The animals are treated with tretazicar at various stages of their development to access the affect of the specific ablation of the cell population being studied. Cell ablation occurs very rapidly, starting as early as 7 h after administration of the prodrug and appears to be independent of a functional p53 (Cui et al, 1999). Examples of the use of this system include the luminal cells of the mammary gland of transgenic mice. Treatment of NTR expressing animals with resulted in a rapid and selective killing of this population of cells whereas the closely associated myoepithelial cells were unaffected. Other examples of selective ablation using this system have been observed in adipocytes (Felmer et al, 2002), astrocytes (Cui et al, 2001) and neurones (Isles et al, 2001; Ma et al, 2002).

The lack of effect on adjacent cell populations is significant. The hydroxylamine is known to be able to migrate short distances and would thus be expected to have an affect on adjacent cells (Bridgewater et al, 1997; Friedlos et al, 1998). In the above experiments the fundamental difference is that the target cell population is dividing while the adjacent tissue probably is not. Activation of tretazicar is known to be effective against non-dividing (non-cycling) cells (Bridgewater et al, 1995). However, this effect can only be measured by allowing these cells to enter division. Thus, what appears to be happening is that tretazicar induced DNA damage (i.e. DNA interstrand crosslinks) is being induced in both dividing and non-dividing cell populations but this only results in cell cytotoxicity when a cell attempts to undergo division whilst its DNA is still damaged. In contrast, S-phase specific agents such as anti-folates only affect cells that are undergoing division while the agent is present.

In the ablation experiments the tissue to be ablated is dividing but the adjoining tissues probably will not—thus the very clean result. The DNA damage is not permanent and it is slowly repaired (Friedlos et al, 1992). The result is a window in which the non-dividing tissues can repair the damage but any cells that enter division will die. The length of this window will depend on the amount of initial DNA damage induced. In cell lines the tretazicar induced crosslink is repaired with a half-life of about 55 hours (Friedlos et al, 1992). This is much longer than other DNA crosslinking agents (Friedlos et al, 1992) and, extrapolating this to the in vivo situation, gives a window (10× half-lives) of about 3 weeks.

In the treatment of cancer a similar situation will exist and non-proliferating tissue should be resistant to the effects of activated tretazicar unless it enters cell division within the window.

Similar arguments can be made for other difunctional alkylating agents and platinating agents. However, they are administered systemically and as a result have a toxic effect on the normal host tissues that are the most rapidly dividing such as bone marrow, gut mucosa and the lymphatic system. As tretazicar is a prodrug this is avoided by the favourable distribution of the activating enzyme (NQO2) or route of administration of the virus (G(V)DEPT). The active 4-hydroxylamine derivative has a very short-half life and cannot migrate very far from the site of activation, so there is no depot effect. Further, most human solid cancers do not have a high proportion of cells that are proliferating at any one-time and the wider killing window, resulting from the relatively poor repair of the tretazicar-induced crosslink, may be an advantage.

A phase I and pharmacokinetic study of tretazicar has been completed previously (Chung-Faye et al, 2001) from which it can be concluded that tretazicar can be safely administered in humans up to 24 mg/m$^2$ without any significant toxicity (the MTD was found to be 37.5 mg/m$^2$).

The use of tretazicar in humans is limited by either the practicality of G(V)DEPT technology or the distribution of NQO2. However, tretazicar could be therapeutically beneficial for treating other cancers (or other diseases of undesirable cell growth or proliferation) if it could be activated in their vicinity. Thus a system for activating tretazicar in, for example, the cervix, bladder, brain, thorax or topically would isolate the activation system from the systemic circulation and allow this to occur. In theory, this could be done by using an enzyme and a co-substrate, although with practical difficulties. However, there are alternative methods for reducing nitro groups. Electrolytic reduction is not realistic in vivo, but nitro groups can be reduced chemically.

Chemical reduction of tretazicar to 5-(aziridin-1-yl)-4-hydroxylamino-2-nitrobenzamide has been reported using either zinc dust and ammonium carbonate in acetone with 13% yield (Knox et al, 1988) or using hydrazine hydrate/Pd—C in tetrahydrofuran with 28% yield (Knox et al, 1993). Neither of these synthetic pathways could be considered for in vivo use.

Similar considerations apply to other reduction-activated prodrugs.

The inventor has now unexpectedly discovered a novel chemical reduction system that allows a reduction activated prodrug to be reduced to a corresponding active substance in, for example, both aqueous solutions and creams. The discovery allows for potential new therapies in which it is desirable to apply the active agent directly to the patient (for example for treatment of certain cancers, pre-cancerous conditions (e.g. lentigo maligna or, particularly, actinic keratoses) and skin diseases such as psoriasis, which is basically overproduction of skin cells).

As is described in detail in the Examples, the inventor has found that a compound of formula I, such as DHA, can be employed to convert a reduction-activated prodrug (such as tretazicar) to a corresponding active substance (e.g., in the case of tretazicar, 5-(aziridin-1-yl)-4-hydroxylamino-2-nitrobenzamide).

Thus, a fifth aspect of the invention provides a composition comprising:
(a) a reduction-activated prodrug, as hereinbefore defined; and
(b) a compound of formula I, as hereinbefore defined.

When the prodrug is tretazicar, for example, such a composition, under suitable conditions discussed below, will over time produce 5-(aziridin-1-yl)-4-hydroxylamino-2-nitrobenzamide which is able to effect the cross-linking of DNA in cells as discussed above.

It will be appreciated that the above-mentioned composition comprising a reduction-activated prodrug and a compound of formula I is conveniently produced by mixing a composition comprising a reduction-activated prodrug and a composition comprising a compound of formula I. Thus, a sixth aspect of the invention provides a kit of parts comprising a first part which contains a reduction-activated prodrug, as hereinbefore defined, and a second part which contains a compound of formula I, as hereinbefore defined.

Typically, the two parts of the kit are compositions which are compatible with each other (eg they both have the same physical form such as creams, aqueous solutions, and gels) and, when mixed, are able to produce a corresponding active agent (e.g., in the case of tretazicar, 5-(aziridin-1-yl)-4-hydroxylamino-2-nitrobenzamide) from the reaction of the reduction-activated prodrug and compound of formula I (e.g. DHA) under suitable conditions.

Such a kit of parts may also be considered to be a therapeutic system which finds uses in combating undesirable cell growth or proliferation as discussed in detail below.

Conveniently, the kit of parts or therapeutic system contains instructions on the use of the reduction-activated prodrug and compound of formula I and, in particular, they contain instructions on combining the parts that contain reduction-activated prodrug and compound of formula I, including the timing of when they are combined before the use of the resultant composition comprising reduction-activated prodrug and compound of formula I in therapy (e.g. in combating undesirable cell growth and proliferation).

Typically, the composition of the fifth aspect of the invention comprising a reduction-activated prodrug and compound of formula I, and the composition of each of the parts of the kit of parts of the sixth aspect of the invention, are pharmaceutical compositions in which the combination of a reduction-activated prodrug and compound of formula I, and separately a reduction-activated prodrug and compound of formula I in the parts of the kit of parts, are combined with a pharmaceutically acceptable carrier.

Similarly, the invention also includes a pharmaceutical composition comprising a compound of formula I, as hereinbefore defined, and a pharmaceutically acceptable carrier and a pharmaceutical composition comprising 5-(aziridin-1-yl)-4-hydroxylamino-2-nitrobenzamide and a pharmaceutically acceptable carrier.

The nature of the pharmaceutical compositions will depend on the way in which they are used in treating a patient and, in particular, will depend on the route of administration to the patient.

Typically, for treating disorders of the skin or of membranes accessible by digitation (such as membrane of the mouth, vagina, cervix, anus and rectum) the composition or pharmaceutical composition according to the fifth aspect of the invention, or the kit of parts or therapeutic system according to the sixth aspect of the invention, is one which is suitable for topical administration. Such pharmaceutical compositions include creams, ointments, lotions, sprays and gels.

Typically, for treating disorders within the body (and, in particular within cavities of the body), the pharmaceutical composition is in the form of a sterile, pyrogen-free aqueous solution or suspension. Typically, the compound of formula I may be in solution. Typically, the reduction-activated prodrug may be formulated as a suspension.

Methods of producing pharmaceutical compositions such as creams, ointments, lotions, sprays and sterile, pyrogen free aqueous solutions or suspensions are well known in the art. For example, ointments may be formulated by suspending or dissolving the components of the composition, kit of parts or therapeutic system in, for example, a mixture with one or more of the following: mineral oil, liquid petrolatum, white petrolatum, propylene glycol, polyoxyethylene polyoxypropylene compound, emulsifying wax and water. Also, for lotions or creams, the components of the composition, kit of parts or therapeutic system may be suspended or dissolved in, for example, a mixture of one or more of the following: mineral oil, sorbitan monostearate, a polyethylene glycol, lanolin, liquid paraffin, white soft paraffin, polysorbate 60, cetyl esters wax, cetearyl alcohol, 2-octyldodecanol, benzyl alcohol and water.

In the present case, it is preferred if the composition or pharmaceutical composition according to the fifth aspect of the invention is mildly alkaline. In relation to the composition comprising a combination of tretazicar and a compound of formula I it is particularly preferred if the composition is mildly alkaline since mild alkalinity favours the production of 5-(aziridin-1-yl)-4-hydroxylamino-2-nitrobenzamide from tretazicar and the compound of formula I, and the combination of tretazicar and the compound of formula I would be non-reactive at neutral or acidic pH.

In relation to the compositions or pharmaceutical compositions that represent the components of the kit of parts or therapeutic system according to the sixth aspect of the invention (i.e. the compositions containing, separately, a reduction-activated prodrug and a compound of formula I), it is particularly preferred that, when they are combined, the resultant combination is mildly alkaline.

It is preferred if the separate compound of formula I component is mildly acidic. It is preferred if the reduction-activated prodrug component is mildly alkaline (particularly for compounds such as tretazicar, which is unstable at acidic pH). It is preferred that the combined product is mildly alkaline.

By "mildly alkaline" we include the meaning that the composition has a pH of 8 to 10.5, more preferably 9 to 10.

It will be appreciated that when the pharmaceutical composition is an aqueous solution, its alkalinity (pH) may be measured directly for example by using pH indicator papers or solutions, or by using a pH electrode. In relation to assessing the alkalinity (pH) of other compositions such as creams, the composition can be mixed or extracted with water and the pH of the aqueous solution produced from the mixing or extraction can be measured.

For example, in relation to a cream the pH of the cream is easily measured by vortexing 0.2 mg of cream with 1 mL of water for 10 seconds. The suspension is cleared by centrifugation and the pH of the water is measured.

The alkalinity of the composition may be controlled by the use of buffers as is well known in the art. Buffers which are physiologically acceptable and approved for use in medicines are also well known in the art.

A preferred buffer system is the combination of sodium bicarbonate ($NaHCO_3$) and sodium carbonate ($Na_2CO_3$). This buffer is particularly suitable for use in a cream.

The inventor has found that by varying the initial buffer concentrations both the duration and extent of the reaction between reduction-activated prodrugs (e.g. tretazicar) and compounds of formula I (e.g. DHA) can be controlled. The pH affects the reaction rate and thus the extent of the reaction over a given period of time. The duration of the reaction can be controlled by the strength of the buffer. Protons appear to be formed by the reaction and these will deplete the buffer. When the buffer is depleted the pH will drop and the reaction will effectively stop. By varying the buffer strength (concentration) the time at which this happens can be altered. Preferably a buffer system is chosen so that when the reduction-activated prodrug and compound of formula I are mixed, 50% of the reaction is completed within 60 minutes.

It is preferred if the composition of the fifth aspect of the invention which comprises a reduction-activated prodrug and a compound of formula I contains a molar excess of the compound of formula I over the reduction-activated prodrug. Similarly, it is preferred if, in the kit of parts or therapeutic system, when the parts are combined there is a molar excess of the compound of formula I over the reduction-activated prodrug. Preferably, the molar excess of the compound of formula I over the reduction-activated prodrug is greater than 4:1, such as >5:1 (compound of formula I: reduction-activated prodrug, e.g. DHA tretazicar), more preferably >10:1.

In the composition or pharmaceutical composition according to the fifth aspect of the invention, or the kit of parts or therapeutic system according to the sixth aspect of the invention, it is preferred that:

(a) the concentration of the reduction-activated prodrug (e.g. tretazicar) in the composition containing said component is in the region of 0.5 to 5% w/w (e.g. 0.5 to 1% w/w) of the composition (e.g. 5 to 10 mg per gram of the composition); and
(b) the concentration of the compound of formula I (e.g. DHA) in the composition containing said component is in the region of 2.5 to 10% w/w (e.g. 5 to 10% w/w) of the composition (e.g. 50 to 100 mg per gram of the composition).

As far as the inventor is aware, nobody has proposed using tretazicar for topical administration, for example in a cream or lotion or ointment, previously. Thus, a further aspect of the invention provides a composition for topical administration comprising tretazicar; preferably, the pharmaceutical composition. The composition may be in the form of a cream or lotion or ointment.

The use of certain compounds of formula I (DHA and glyceraldehyde) for medical treatments (the treatment of microbial infections or for killing cancer cells) is disclosed in WO 2006/003492, *Naturwissenschaften* 51, 217-218 (1964) and *Cancer Chemother. Rep.* (Part 1) 52(7), 687-696 (1968). However, as far as the inventor is aware, nobody has proposed previously that a compound of formula I other than DHA or glyceraldehyde can be used in medicine. Thus a further aspect of the invention provides a compound of formula I, as hereinbefore defined, for use in medicine, provided that the compound is not DHA or glyceraldehyde. The compound of formula I is packaged and presented for use in medicine.

The invention also includes a pharmaceutical composition comprising a compound of formula I, as hereinbefore defined, and a pharmaceutically acceptable carrier, provided that the compound is not DHA or glyceraldehyde. In one embodiment, the pharmaceutical composition is not a cream or lotion or ointment or spray. It is preferred if the pharmaceutical composition comprising the compound of formula I is a sterile, non-pyrogenic injectable aqueous solution.

Although 5-(aziridin-1-yl)-4-hydroxylamino-2-nitrobenzamide is known as the product of the nitro-reduction of tretazicar, as far as the inventor is aware, nobody has proposed that a composition, such as a pharmaceutical composition as discussed above, containing it could be used in medicine. Thus, a still further aspect of the invention provides 5-(Aziridinyl-1-yl)-4-hydroxylamino-2-nitrobenzamide for use in medicine.

As detailed above, the fourth aspect of the invention relates to a method of reducing a reduction-activated prodrug, the method comprising contacting the reduction-activated prodrug with a compound of formula I, as hereinbefore defined. Typically, the reduction-activated prodrug and compound of formula I are contacted in a suitable aqueous solution. Preferably, the solution is mildly alkaline as described above.

The inventor has found that, when this method is carried out with tretazicar and DHA, carrying out the reaction at pH 9 gives a faster rate of reduction than at pH 10 and gives mostly the preferred 4-hydroxylamine product (compared to the 2-hydroxylamine product) in very high yield. Also preferably in these methods there is a molar excess of compound of formula I over reduction-activated prodrug and the range and preferred molar excess is as described above. When applied to the reaction of tretazicar with compounds of formula I, the methods may also contain the further step of purifying the 5-(aziridin-1-yl)-4-hydroxylamino-2-nitrobenzamide product from the reaction mixture, for example by using any suitable separation method such as HPLC.

It is notable that nitro groups in compounds such as tretazicar are reduced solely to a hydroxylamine group (and to no other group, such as to a nitroso or amine group).

Thus, according to a further aspect of the invention, there is provided the use of a compound of formula I, as hereinbefore defined, for the selective reduction of an organic nitro compound to the corresponding hydroxylamine. In a particular embodiment of this aspect of the invention, the use is of a compound of formula I and base. The identity and quantity of the base employed, as well as the pH at which the compound of formula I effects reduction of the nitro compound, may be as defined in respect of the use of the first aspect of the invention.

Similarly, the invention also provides a method for selectively reducing an organic nitro compound to the corresponding hydroxylamine, said method comprising contacting said organic nitro compound with a compound of formula I, as hereinbefore defined. In a particular embodiment, the method comprises contacting the organic nitro compound with a compound of formula I and base. The identity and quantity of the base employed may be as defined in respect of the use of the first aspect of the invention. Further, in another particular embodiment, the method comprises contacting the organic nitro compound with a compound of formula I, as hereinbefore defined, in the presence of a solution (e.g. an aqueous solution) or suspension having a pH of between 7 and 11 (e.g. a pH from 7.1 (such as 7.2, 7.3, 7.4 or 7.5) to 10.9 (such as 10.8, 10.7, 10.6, 10.5, 10.4, 10.3, 10.2, 10.1 or 10.0)).

The organic nitro compound may be, for example, any of the nitro compounds described hereinbefore. Particularly, however, the organic nitro compound is an aromatic or heteroaromatic nitro compound.

When used herein, the term "aromatic nitro compound" includes references to compounds comprising a $C_{6-14}$ carbocyclic aromatic group (e.g. a phenyl, naphthyl, anthracenyl or phenanthrenyl group), which aromatic group bears a nitro substituent. In addition to bearing a nitro substituent, the aromatic group is optionally further substituted by one or more substituents selected from $C_{1-6}$ alkyl, $C_{1-6}$ alkoxy (which latter two groups are optionally substituted by one or more substituents selected from halo, OH, $C_{1-4}$ alkoxy, Het and aryl), OH, halo (such as a fluoro, chloro, bromo or iodo), cyano, nitro, $CO_2R^a$, $C(O)NR^bR^c$, $S(O)_{1-2}R^d$, $S(O)_2NR^bR^c$, $N(R^b)R^c$, Het, aziridinyl and aryl, wherein $R^a$ to $R^d$ independently represent $C_{1-6}$ alkyl (optionally substituted by one or more substituents selected from halo, OH, $C_{1-4}$ alkoxy, Het and aryl), Het or aryl, or $R^a$ to $R^c$ may alternatively (and independently) represent H, and wherein Het and aryl are as hereinbefore defined.

In particular embodiments, the carbocyclic aromatic group bears at least one further electron-withdrawing substituent, for example one or more (e.g. one or two) substituents selected from halo (such as a fluoro, chloro, bromo or iodo), cyano, nitro, $CO_2R^a$, $C(O)NR^bR^c$, $S(O)_{1-2}R^d$ and $S(O)_2NR^bR^c$, wherein $R^a$ to $R^d$ are as hereinbefore defined. As will be appreciated by those skilled in the art, the substitution pattern of a carbocyclic aromatic group will govern the reduction potential of a nitro moiety attached to that group. Generally, the addition of electron-withdrawing substituents to that group would be expected to increase (i.e. make less negative) the reduction potential ($E^2$ or $E^0$, as measured, for example, by polarography). In a still more particular embodiment, the carbocyclic aromatic group bears at least one further nitro substituent.

When used herein, the term "heteroaromatic nitro compound" includes references to compounds comprising a 5- to 14-membered heteroaromatic group containing one or more heteroatoms selected from oxygen, nitrogen and/or sulfur, which heteroaromatic group may comprise one, two or three rings and which heteroaromatic group bears a nitro substituent. The heteroaromatic group optionally bears one or more substituents selected from $C_{1-6}$ alkyl, $C_{1-6}$ alkoxy (which latter two groups are optionally substituted by one or more substituents selected from halo, OH, $C_{1-4}$ alkoxy, Het and aryl), OH, oxo, halo (such as a fluoro, chloro, bromo or iodo), cyano, nitro, $CO_2R^a$, $C(O)NR^bR^c$, $S(O)_{1-2}R^d$, $S(O)_2NR^bR^c$, $N(R^b)R^c$, Het, aziridinyl and aryl, wherein $R^a$ to $R^d$ are as hereinbefore defined. For the avoidance of doubt, the term "heteroaromatic nitro compound" includes references to part-aromatic heterocyclic groups comprising two or three rings, in which at least one ring (but not all rings) is aromatic. In these ring systems, it is preferred that the nitro group is attached to the aromatic ring.

Particular heteroaromatic ring systems that may be mentioned in connection with the term "heteroaromatic nitro compound" include benzimidazolyl, benzo[c]isoxazolidinyl, benzisoxazolyl, benzofuranyl, benzofurazanyl, 2,1,3-benzoxadiazolyl, benzoxazolyl, benzopyrazolyl, benzo[e]pyrimidine, 2,1,3-benzothiadiazolyl, benzothiazolyl, benzothienyl, benzotriazolyl, cinnolinyl, furanyl, imidazolyl, imidazo[1,2-a]pyridinyl, imidazo[2,3-b]thiazolyl, indolyl, isoquinolinyl, isoxazolyl, naphtho[1,2-b]furanyl, oxadiazolyl, oxazolyl, phthalazinyl, purinyl, pyrazinyl, pyrazolyl, pyridinyl, pyrimidinyl, pyrrolo[2,3-b]pyridinyl, pyrrolo[5,1-b]pyridinyl, pyrrolo[2,3-c]pyridinyl, pyrrolyl, quinazolinyl, quinolinyl, thiadiazolyl, thiazolyl, thienyl, thieno[5,1-c]pyridinyl, triazolyl, 1,3,4-triazolo[2,3-b]pyrimidinyl, xanthenyl, benzodioxanyl, benzodioxepanyl, benzodioxolyl, benzomorpholinyl, benzoxazolidinyl, chromanyl, chromenyl, 2,3-dihydrobenzimidazolyl, 2,3-dihydrobenzo[b]furanyl, 1,3-dihydrobenzo[c]furanyl, 1,3-dihydro-2,1-benzisoxazolyl 2,3-dihydropyrrolo-[2,3-b]pyridinyl, 4,5,6,7-tetrahydrobenzimidazolyl, 4,5,6,7-tetrahydrobenzopyrazolyl, 5,6,7,8-tetrahydrobenzo[e]pyrimidine, thiochromanyl and the like.

The inventor has surprisingly found that reduction of reducible compounds (e.g. reducible organic compounds, such as organic nitro compounds or reduction-activated prodrugs) by a compound of formula I, as hereinbefore defined, may be effectively performed by adding the compound of formula I to a pre-formed mixture (e.g. solution or suspension) of the reducible compound and base.

Thus, according to a further aspect of the present invention, there is provided a method of reducing a reducible compound, said method comprising adding a compound of formula I, as hereinbefore defined, to a mixture of said reducible compound and base, wherein the base is as hereinbefore defined in respect of the first aspect of the invention.

The reducible compound may be a reducible organic compound, such as an organic nitro compound or a reduction-activated prodrug, as hereinbefore defined (e.g. tretazicar). In this aspect of the invention, the compound of formula I may be, in particular, DHA.

The mixture of reducible compound and base may be, for example, a solution or suspension in an aqueous or, particularly, an organic solvent system. Particular solvent systems that may be mentioned in this respect include lower ($C_{1-4}$) alkyl alcohols (such as isopropanol, ethanol or methanol), chlorinated hydrocarbons (such as dichloromethane), water and mixtures thereof (either mono- or bi-phasic mixtures). Particular bases that may be mentioned include alkali (e.g. sodium or potassium) metal bicarbonates or, particularly, carbonates (e.g. potassium carbonate, such as anhydrous potassium carbonate).

The reduction may be carried out at, for example, ambient temperature or above. In particular embodiments of the invention, the reaction is carried out at elevated temperature (e.g. above 25° C.), such as at between 30 and 100° C. (e.g. from 40 to 70° C., such as at about 60° C.). The reduction may also be carried out in the substantial absence of oxidising agents, such as atmospheric oxygen. Thus, in particular embodiments of the invention, the reaction is carried out under an inert atmosphere (e.g. a nitrogen or argon atmosphere) and/or using deoxygenated (or degassed) solvents and/or reagents.

In a more particular embodiment of the invention, the reducible compound is maintained in a stoichiometric excess in comparison to the calculated number of moles of the compound of formula I required to effect the desired reduction. In this respect, and without wishing to be bound by theory, it is believed that the compounds of formula I provide one mole of hydride equivalent per mole of dimer of formula Ia (i.e. one mole of hydride equivalent per two moles of compound of formula I). Thus, for example, for the reduction of nitro to hydroxylamine (a two-electron reduction requiring the provision of two hydride equivalents), the number of moles of the compound of formula I required to effect the desired reduction is four moles per mole of nitro compound.

The compound of formula I may be added at any rate to the mixture of reducible compound and base. However, in certain embodiments of the invention, the compound of formula I is added to the mixture slowly, such as at most 2 molar equivalents (relative to the reducible compound) per minute (e.g. at most 1.75, 1.5, 1.25, 1.0, 0.9, 0.8, 0.7, 0.6, 0.5, 0.4, 0.3 or, particularly, 0.2 or 0.15 molar equivalents per minute).

As mentioned above, the reducible compound may be tretazicar. Thus, a particular embodiment of this aspect of the invention relates to a method of preparing 5-(aziridin-1-yl)-4-hydroxylamino-2-nitrobenzamide (or 5-(aziridin-1-yl)-2-hydroxylamino-4-nitrobenzamide), said method comprising:
(a) providing a mixture of tretazicar and base; and
(b) adding at most four molar equivalents of a compound of formula I (or, in the alternative, at most two molar equivalents of the dimeric form of a compound of formula I (i.e. a compound of formula Ia)).

The compound of formula I may, in a particular embodiment, be DHA.

This reaction may be carried out under the conditions (and using the base and/or solvents) described above in relation to the method of reducing a reducible compound. Further embodiments of this aspect of the invention include those in which the method comprises the further step of separating the product 5-(aziridin-1-yl)-4-hydroxylamino-2-nitrobenzamide from the co-product 5-(aziridin-1-yl)-2-hydroxylamino-4-nitrobenzamide), if produced. Separation may be effected by techniques known to those skilled in the art (e.g. fractional crystallisation, recrystallisation, chromatography, solvent extraction, vacuum sublimation, etc.).

A further aspect of the invention provides a method of combating undesirable growth or proliferation of cells at a site in an individual the method comprising providing a reduction-activated prodrug of an antiproliferative agent (e.g. tretazicar) and a compound of formula I, as hereinbefore defined, at the said site in the individual.

When used herein, the term "reduction-activated prodrug of an antiproliferative agent" includes reference, in particular, to the reduction-activated prodrugs identified hereinbefore, such as Mitomycin C, E09, RSU-1069, RB-6145 and, particularly, tretazicar.

The reduction-activated prodrug and compound of formula I may be combined before administration to the individual or they may be administered sequentially.

For example, in relation to topical administration, it is convenient to combine a composition containing the reduction-activated prodrug and a composition containing the compound of formula I (in both cases the composition being ones which are suitable for topical administration) before administration to the individual. This embodiment is described in more detail (with reference to the combination of tretazicar and DHA) in the case where the composition for topical administration is a cream in Examples 2 and 3 below.

Similarly, in relation to administration into a body cavity, conveniently a composition containing the reduction-activated prodrug and a composition containing the compound of formula I (in both cases the composition being ones which are suitable for administration into a body cavity) are combined before administration. However, it is also possible for the combination to take place within the body cavity (for example, separate sterile, non-pyrogenic solutions or suspensions of the reduction-activated prodrug and the compound of formula I could be administered into the body cavity and the initial contacting of the reduction-activated prodrug and the compound of formula I would occur in the body cavity. In one embodiment, the reduction-activated prodrug and the compound of formula I may be co-administered under, for example, neutral conditions and a further administration of an agent (such as a buffer) made to make the environment in the body cavity mildly alkaline. Typically, however, the reduction-activated prodrug (or its combination with the compound of formula I) is present in an alkaline medium.

It will be appreciated that when the reduction-activated prodrug and the compound of formula I are combined under suitable conditions before administration to the individual, a corresponding active substance (e.g., in the case of tretazicar, 5-(aziridin-1-yl)-4-hydroxylamino-2-nitrobenzamide) is produced which is then administered to the individual. Thus, a still further aspect of the invention provides a method of combating undesirable growth or proliferation of cells at a site in an individual the method comprising administering or providing a composition containing 5-(aziridin-1-yl)-4-hydroxylamino-2-nitrobenzamide at the said site in the individual.

Still further aspects of the invention provide:
(i) use of a combination of a reduction-activated prodrug of an antiproliferative agent, as hereinbefore defined, and a compound of formula I, as hereinbefore defined, in the manufacture of a medicament for combating undesirable growth or proliferation of cells in an individual; and
(ii) use of 5-(aziridin-1-yl)-4-hydroxylamino-2-nitrobenzamide in the manufacture of a medicament for combating undesirable growth or proliferation of cells in an individual.

Corresponding aspects of the invention relate to a method of treating an undesirable growth or proliferation of cells, said method comprising administering to a patient in need of such treatment:
(i) a combination product comprising a reduction activated prodrug of an antiproliferative agent, or a pharmaceutically acceptable salt and/or solvate thereof, and a compound of formula I; or
(ii) an effective amount of 5-(aziridin-1-yl)-4-hydroxylamino-2-nitrobenzamide.

The combination product may be either a kit-of-parts or a combined preparation. Thus, this aspect of the invention encompasses the administration to the patient of:
(a) a composition comprising
 (I) a reduction-activated prodrug of an antiproliferative agent, or a pharmaceutically acceptable salt and/or solvate thereof,
 (II) a compound of formula I, as hereinbefore defined and, optionally
 (III) a pharmaceutically acceptable adjuvant, diluent or carrier; or
(b) a kit-of-parts comprising
 (I) a first part which contains a reduction-activated prodrug of an antiproliferative agent, or a pharmaceutically acceptable salt and/or solvate thereof, and
 (II) a second part which contains a compound of formula I, as hereinbefore defined.

Still further aspects of the invention relate to the combination product (i.e. composition or kit-of-parts) per se. In these aspects of the invention, the reduction-activated prodrug of an antiproliferative agent is as hereinbefore defined.

Typically, the two parts of the kit-of-parts are compositions which are compatible with each other (e.g. they both have the same physical form such as creams, aqueous solutions, and gels) and, when mixed, are able to produce a corresponding active agent (e.g., in the case of tretazicar, 5-(aziridin-1-yl)-4-hydroxylamino-2-nitrobenzamide) from the reaction of the reduction-activated prodrug and compound of formula I (e.g. DHA) under suitable conditions.

Such a kit of parts may also be considered to be a therapeutic system which finds uses in combating undesirable cell growth or proliferation.

Conveniently, the kit-of-parts or therapeutic system contains instructions on the use of the reduction-activated prodrug of an antiproliferative agent and compound of formula I and, in particular, they contain instructions on combining the parts that contain reduction-activated prodrug of an antiproliferative agent and compound of formula I, including the timing of when they are combined before the use of the resultant composition comprising reduction-activated prodrug and compound of formula I in therapy (e.g. in combating undesirable cell growth and proliferation).

Typically, the composition comprising a reduction-activated prodrug of an antiproliferative agent and compound of formula I, and the composition of each of the parts of the kit-of-parts, are pharmaceutical compositions in which the combination of a reduction-activated prodrug of an antiproliferative agent and compound of formula I, and separately a reduction-activated prodrug of an antiproliferative agent and compound of formula I in the parts of the kit-of-parts, are combined with a pharmaceutically acceptable carrier.

In treating the undesirable growth or proliferation of cells, the combination product (combined composition or kit-of-parts) or 5-(aziridin-1-yl)-4-hydroxylamino-2-nitrobenzamide may be administered as the sole therapeutic system or agent or, alternatively, may be administered in conjunction with (i.e. either concomitantly or sequentially) with one or more further active agents (e.g. active agents known for treating the particular disorder in question).

The undesirable growth or proliferation of cells to be combated may be any such undesirable growth or proliferation, particularly those which are susceptible to cross-linking of their DNA.

The undesirable growth or proliferation of cells may be benign such as is the case with common warts or psoriasis or other skin conditions which involve undesirable growth or proliferation of cells, or it may be neoplastic, such as in a tumour or metastasis thereof.

Thus, methods and medicaments of the invention (i.e. those including a reduction-activated prodrug of an antiproliferative agent, 5-(aziridin-1-yl)-4-hydroxylamino-2-nitrobenzamide, or the use of either) may be used in the treatment of warts and other skin diseases such as psoriasis. Other benign growths, pre-cancerous conditions and cancer, including cancer of the cervix, bladder, brain, thorax and uterus.

It is particularly preferred if the methods and medicaments are used topically to combat disease.

It is also particularly preferred if the methods and medicaments are used for combating disease by administration into body cavities such as the bladder or peritoneum or thorax. With respect to tretazicar, its active 4-hydroxylamine derivative has a very short half-life after application or delivery and cannot migrate very far from the site of activation, so there is no depot effect and the active drug does not enter the circulation and cause systemic effects.

Particular embodiments of the invention that may be mentioned therefore include:
(a) a topical composition (e.g. cream, lotion or ointment) comprising a reduction-activated prodrug of an antiproliferative agent (e.g. RSU-1069, Mitomycin C or, particularly, tretazicar or E09), a compound of formula I (e.g. DHA) and a topically-acceptable adjuvant, diluent or carrier (e.g. a lotion, cream or ointment base);
(b) a pellet or similar solid delivery vehicle comprising a reduction-activated prodrug of an antiproliferative agent (e.g. RSU-1069, Mitomycin C or, particularly, tretazicar or E09), a compound of formula I (e.g. DHA) and a pharmaceutically-acceptable adjuvant, diluent or carrier; and
(c) a solution or suspension comprising a reduction-activated prodrug of an antiproliferative agent (e.g. RSU-1069, Mitomycin C or, particularly, tretazicar or E09), a compound of formula I (e.g. DHA) and a pharmaceutically-acceptable adjuvant, diluent or carrier (e.g. a sterile solvent system, such as a sterile aqueous solvent system).

In relation to (a) and (b) above, the particular composition may also comprise base (e.g. a base as defined above in relation to the first aspect of the invention) and/or a pH buffering system that, upon application of the composition, provides a local pH at the site of administration of between 7 and 11 (for example: for formulations containing tretazicar, between pH 7.5, 8.0, 8.5 or 9.0 and 10.5 or, particularly, 10; or form formulations containing E09 between pH 7.1 and 8.0, such as about pH 7.5).

The topical composition (or cream, lotion or ointment) of (a) above may be employed, for example, in the treatment of skin cancer, non-melanomas on skin, prostate cancer, pre-cancerous conditions (e.g. lentigo maligna or, particularly, actinic keratoses), warts or psoriasis. Such a composition may also be employed as a rectal cream in the treatment of conditions such as bowel cancer.

The solid delivery vehicle of (b) above may, when it comprises E09, be particularly suited to use in the treatment of prostate cancer. This is because the prostate gland is known to be particularly sensitive to high pH levels, and E09 has been found by the present inventor to be more rapidly reduced at relatively low pH (e.g. about pH 7.5) than compounds such as tretazicar.

The solution or suspension of (c) above may be deployed by injection, transcatheterisation or other infusion method into a body cavity or space in which there exists an undesirable growth or proliferation of cells. For example, the solution may be introduced into the bladder to treat conditions such as bladder cancer, brought into contact with the cervix to treat cervical cancer, injected into the peritoneum to treat, for example, cancer of the ovary, or may be injected into the brain to treat brain cancer.

In a particular embodiment, a solution or suspension comprising a compound of formula I (e.g. DHA) and a reduction-activated prodrug of an antiproliferative agent (e.g. tretazicar or E09) may be administered by intravesical urinary catheter infusion in order to treat bladder cancer.

Thus, a further aspect of the invention relates to a method of treating bladder cancer, said method comprising administering, by intravesical urinary catheter infusion, an effective amount of a solution or suspension comprising compound of formula I (e.g. DHA) and a reduction-activated prodrug of an antiproliferative agent (e.g. tretazicar or E09).

The composition described above comprising 5-(aziridin-1-yl)-4-hydroxylamino-2-nitrobenzamide may also take particular pharmaceutical forms, such as:
(i) a topical composition (e.g. cream, lotion or ointment) comprising 5-(aziridin-1-yl)-4-hydroxylamino-2-nitrobenzamide and a topically-acceptable adjuvant, diluent or carrier (e.g. a lotion, cream or ointment base); and
(ii) a solution or suspension comprising 5-(aziridin-1-yl)-4-hydroxylamino-2-nitrobenzamide and a pharmaceutically-acceptable adjuvant, diluent or carrier (e.g. a sterile solvent system, such as a sterile aqueous solvent system).

Compositions (i) and (ii) above may have the same ultimate uses as described in relation to compositions (a) and (c) above, respectively.

Alternatively, the solution or suspension of (ii) above (as well as the solution or suspension of (c) above) may be administered by way of a spray to the mouth, nasal cavity, throat, pharynx, larynx, trachea or lungs in order to treat an undesirable proliferation of cells (e.g. a cancer) at any one of those locations. Thus, a further aspects of the invention relate to a sprayable solution or suspension comprising:
(A) a reduction-activated prodrug of an antiproliferative agent, a compound of formula I, as hereinbefore defined, and a pharmaceutically-acceptable adjuvant, diluent or carrier; or
(B) 5-(aziridin-1-yl)-4-hydroxylamino-2-nitrobenzamide and a pharmaceutically-acceptable adjuvant, diluent or carrier.

Administration, by way of a spray, of 5-(aziridin-1-yl)-4-hydroxylamino-2-nitrobenzamide (or a mixture providing that compound) directly to the mouth, nasal cavity, throat, pharynx, larynx, trachea or lungs circumvents deactivation of 5-(aziridin-1-yl)-4-hydroxylamino-2-nitrobenzamide by serum proteins. Moreover, the same deactivation mechanism will ensure that 5-(aziridin-1-yl)-4-hydroxylamino-2-nitrobenzamide will not have a systemic effect.

Thus, a still further aspect of the invention relates to a method of treating a cancer of the mouth, nasal cavity, throat, pharynx, larynx, trachea or lungs, said method comprising administering, by way of a spray, a solution or suspension comprising:
(A) a reduction-activated prodrug of an antiproliferative agent, a compound of formula I, as hereinbefore defined, and a pharmaceutically-acceptable adjuvant, diluent or carrier; or
(B) 5-(aziridin-1-yl)-4-hydroxylamino-2-nitrobenzamide and a pharmaceutically-acceptable adjuvant, diluent or carrier.

Devices suitable for delivering a solution or suspension in the form of a spray are well known to those skilled in the art. Suitable devices (including: mechanical sprayers that pump the solution or suspension from a reservoir; and aerosol devices that utilise compressed propellant gases to generate a spray through a nozzle) include those described in, for example, WO 2006/005845.

Thus, further aspect of the invention relate to:
(a) a mechanical sprayer having a reservoir loaded with a solution or suspension comprising
   a reduction-activated prodrug of an antiproliferative agent, a compound of formula I, as hereinbefore defined, and a pharmaceutically-acceptable adjuvant, diluent or carrier, or
   5-(aziridin-1-yl)-4-hydroxylamino-2-nitrobenzamide and a pharmaceutically-acceptable adjuvant, diluent or carrier; and
(b) an aerosol device comprising a solution or suspension comprising one or more propellant gases and
   a reduction-activated prodrug of an antiproliferative agent, a compound of formula I, as hereinbefore defined, and a pharmaceutically-acceptable adjuvant, diluent or carrier, or
   5-(aziridin-1-yl)-4-hydroxylamino-2-nitrobenzamide and a pharmaceutically-acceptable adjuvant, diluent or carrier.

The device described in (b) above may be, in one embodiment, a metered dose inhaler device.

As an alternative to a liquid spray, a dry powder can be aerosolised in order to deliver a pharmaceutical to sites such as the lungs. Thus, according to a further aspect of the invention, there is provided a dry powder aerosol composition comprising 5-(aziridin-1-yl)-4-hydroxylamino-2-nitrobenzamide.

By the term "dry powder aerosol composition", we include references to dry powder formulations that are capable of being delivered by an inhalation device to the mouth, nasal cavity, throat, pharynx, larynx, trachea or lungs. As such, the term includes references to dry powders having an average particle size of 100 μm (e.g. 50 or 10 μm) or less. In this respect, particle size may be determined by methods known to those skilled in the art (e.g. by laser light scattering techniques, such as those using a particle size analysis device such as a Mastersizer™).

Devices for the delivery of dry powder aerosols (e.g. dry powder inhalers) are well known to those skilled in the art and are described, for example, in WO 2004/110536. Thus, according to a further aspect of the invention, there is provided a therapeutic system comprising:
(i) a dry powder inhalation device, optionally containing a source of propellant gas; and
(ii) one or more discrete doses of a dry powder aerosol composition comprising 5-(aziridin-1-yl)-4-hydroxylamino-2-nitrobenzamide.

The therapeutic system may comprise the device and dose (s) of composition as physically separate entities (i.e. effectively as a kit-of-parts). Alternatively, the inhalation device may be pre-loaded with the one or more doses of composition.

In treating the undesirable growth or proliferation of cells, the above-mentioned compositions (including topical compositions, solid delivery vehicles, solutions or suspensions, dry powder aerosols, etc.) may be used alone for the treatment of a particular condition (an undesirable growth or proliferation of cells, such as a cancer of the bladder, cervix, peritoneum or brain, or a cancer of the mouth, nasal cavity, throat, pharynx, larynx, trachea or lungs), i.e. administered as the sole therapeutic system or agent. Alternatively, however, the compositions may be administered in conjunction (i.e. either concomitantly or sequentially) with one or more further active agents (e.g. active agents known for treating the particular disorder in question).

In this respect, active agents known for use in the treatment of bladder cancer include cisplatin, doxorubicin and mitomycin C.

Suitable doses of reduction-activated prodrug (e.g. tretazicar) for human use include 10 to 30 mg/m$^2$, typically 15 to 25 mg/m$^2$ for example 24 mg/m$^2$.

The methods and medicaments of the invention can be used to treat animals (such as non-human mammals, in particular horses, cows, sheep and the like, and cats and dogs) and humans. It is preferred if they are used to treat humans.

A further aspect of the invention provides a method of cross-linking DNA in a cell the method comprising administering to the cell a combination of a reduction-activated prodrug of a DNA cross-linking agent (e.g. tretazicar) and a compound of formula I, as hereinbefore defined (e.g. DHA), or a method of cross-linking DNA in a cell the method comprising administering to the cell a composition which includes 5-(aziridinyl-1-yl)-4-hydroxylamino-2-nitrobenzamide. Typically, the cell is a cell in culture and the method is an in vitro method.

When used herein, the term "reduction-activated prodrug of a DNA cross-linking agent" includes reference, in particular, to compounds such as:
(1) E09 (3-[5-aziridinyl-4,7-dioxo-3-hydroxymethyl-1-methyl-1H-indol-2-yl]-prop-β-ene-α-ol);
(2) RSU-1069 (1-(1-aziridinyl)-3-(2-nitro-1-imidazolyl)-2-propanol);
(3) RB-6145 (1-[3-(2-bromoethylamino)-2-hydroxypropyl]-2-nitroimidazole);
(4) Mitomycin C;
(5) a compound of the formula

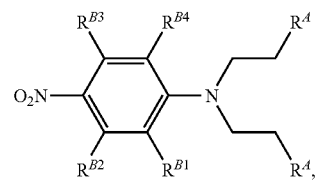

wherein
each R$^A$ independently represents chloro, bromo, iodo or —OS(O)$_2$R$^C$, $R^C$ represents $C_{1-8}$ alkyl (optionally substituted by one or more fluoro atoms) or phenyl (optionally substituted by one or more substituents selected from halo, nitro, $C_{1-4}$ alkyl and $C_{1-4}$ alkoxy), $R^{B1}$ to $R^{B4}$ independently represent H, CN, $C(O)N(R^D)R^E$, $C(S)N(R^D)R^E$, $C(O)OH$, $S(O)_2NHR^F$, or $R^{B1}$ may additionally represent $NO_2$, $R^D$ and $R^E$ independently represent H or $C_{1-4}$ alkyl (which latter group is optionally substituted by one or more substituents selected from OH, N(H)—$C_{1-2}$ alkyl, $N(C_{1-2}$ alkyl$)_2$, 4-morpholinyl and C(O)OH), or $R^D$ and $R^E$, together with the N-atom to which they are attached, represent 4-morpholinyl, and $R^F$ represents H or $S(O)_2CH_3$, provided that $R^{B2}$ is H when $R^{B1}$ is other than H, for example, any one of the compounds of the above formula disclosed in Anlezark et al., 1992 and 1995, such as SN 23163, SN 23849, SN 23777, SN 23428, SN 23759, SN 24927, SN 24928, SN 24926, SN 25402, SN 25079, SN 24939, SN 24935, SN 25923, SN 25313, SN 23856, SN 25066, SN 23816, SN 25015, SN 24971, SN 25260, SN 25261, SN 25263, SN 25084, SN 25188, SN 25507 or, particularly, SN 23862 (5-{N,N-bis[2-chloroethyl]amine}-2,4-dinitrobenzamide);

(6) a compound of the formula

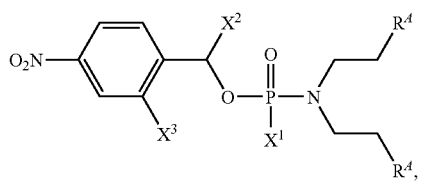

wherein $R^A$ is as defined above (e.g. Cl) and either $X^1$ represents $NH_2$ and $X^2$ and $X^3$ both represent H, —$X^1$—$X^2$— represents —NH—$CH_2CH_2$— and $X^3$ represents H or —$X^1$—$X^3$— represents —NH— and $X^2$ represents H;

(7) a compound of the formula

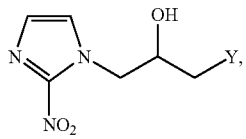

wherein Y represents 1-aziridinyl (optionally substituted at the 2-position by methyl), methoxy or $N(H)CH_2CH_2Br$;

(8) a self-immolative prodrug of the formula

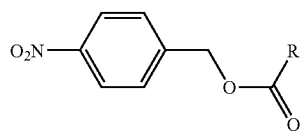

wherein

R represents —O—R' or —NH—R',

R' represents

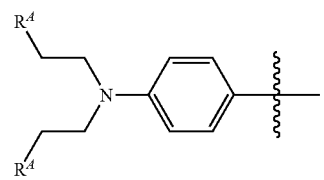

in which the wavy line indicates the position of attachment of the fragment and $R^A$ is as defined above (e.g. Cl);

(9) acridine-CB 1954

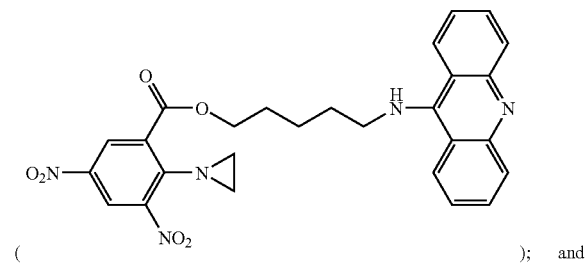 [SMILES: O=C(OCCCCCNc1c2ccccc2nc2ccccc12)c1cc([N+](=O)[O-])cc([N+](=O)[O-])c1N1CC1]

(10) tretazicar (5-(aziridin-1-yl)-2,4-dinitrobenzamide), or a pharmaceutically acceptable salt and/or solvate thereof.

Indeed, the term "reduction-activated prodrug of a DNA cross-linking agent" includes particular reference to compounds such as E09, RSU-1069, RB-6145, Mitomycin C and, particularly, tretazicar.

The invention will now be described in more detail by reference to the following Figures and Examples wherein FIG. 1 shows the structure of tretazicar (5-(aziridin-1-yl)-2,4-dinitrobenzamide).

FIG. 2 shows the bioactivation of tretazicar.

FIG. 3 shows the structure of dihydroxyacetone (DHA; CAS No: 62147-49-3, Beil. 8, 266, Merck Index 13, 3166). The normal form is the dimer, but this rapidly reverts to the monomer in solution.

Figure 5:
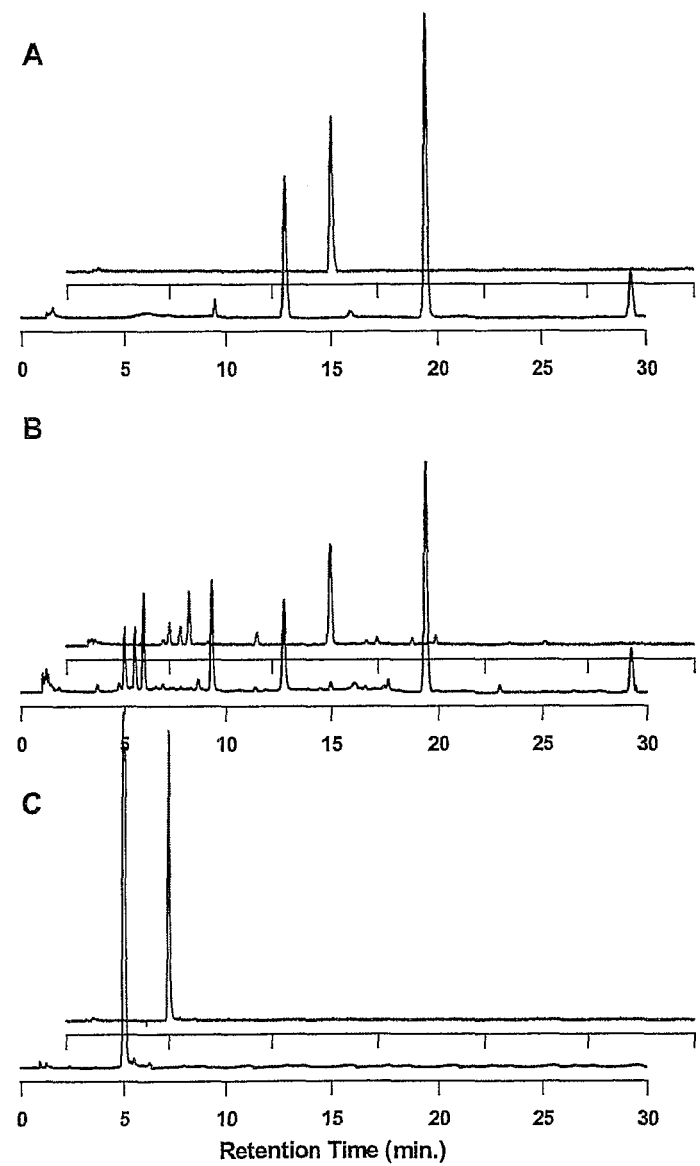
FIG. 5 shows the reduction of tretazicar by DHA in an E45 based cream (as described in Example 2 below). In each of A, B and C of FIG. 5, the upper of the two traces is that measured at 325 nm, whereas the lower is that measured at 260 nm.
Figure 6:
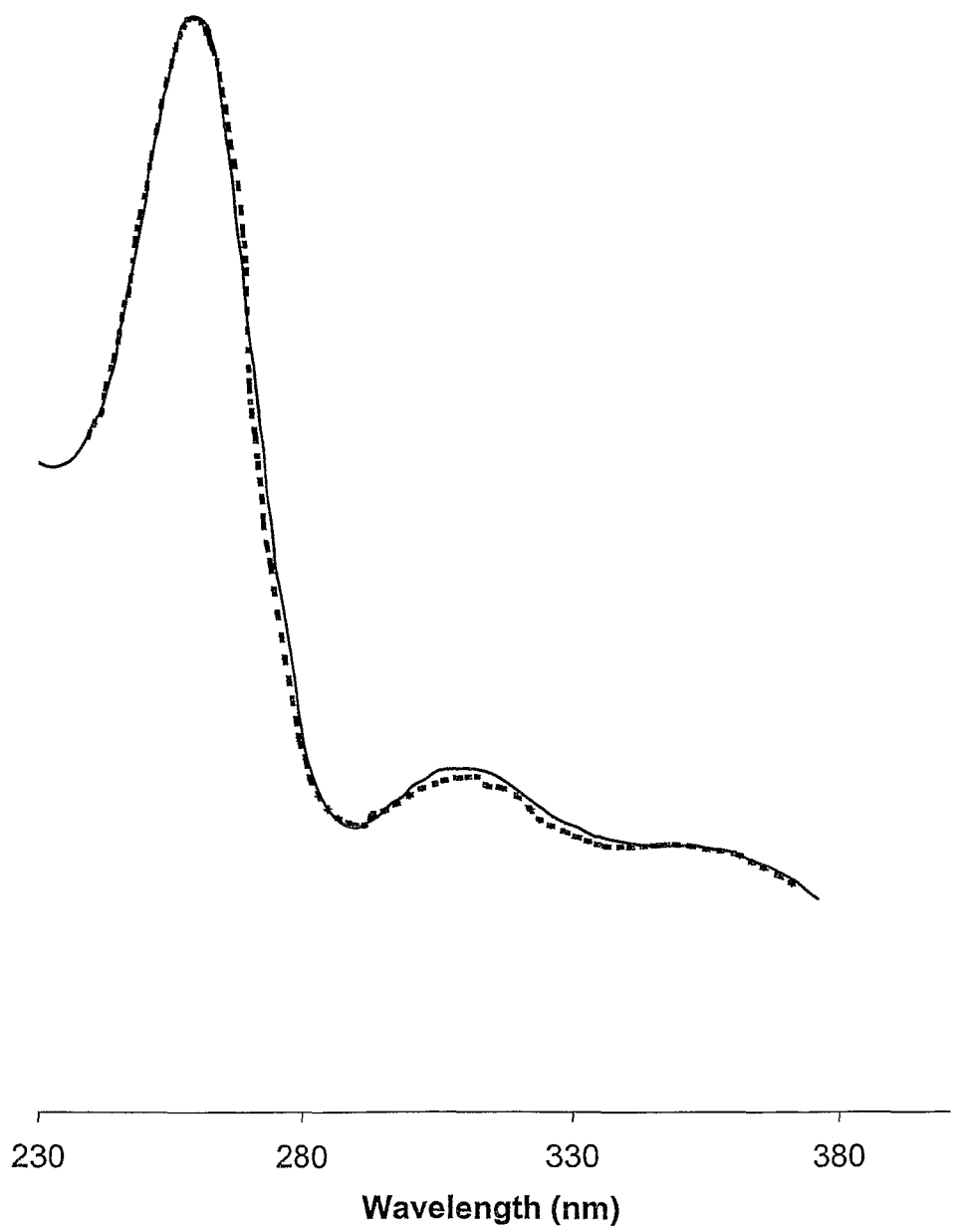

FIG. 6 shows the spectral matching of the peak seen with a retention time of 5.0 minute in FIG. 5B, with that obtained with a synthetic standard of 5-(aziridin-1-yl)-4-hydroxylamino-2-nitrobenzamide. The continuous line is the standard and the dashed line is the sample. The spectra are normalised for absorbance at 260 nm.

Figure 7:
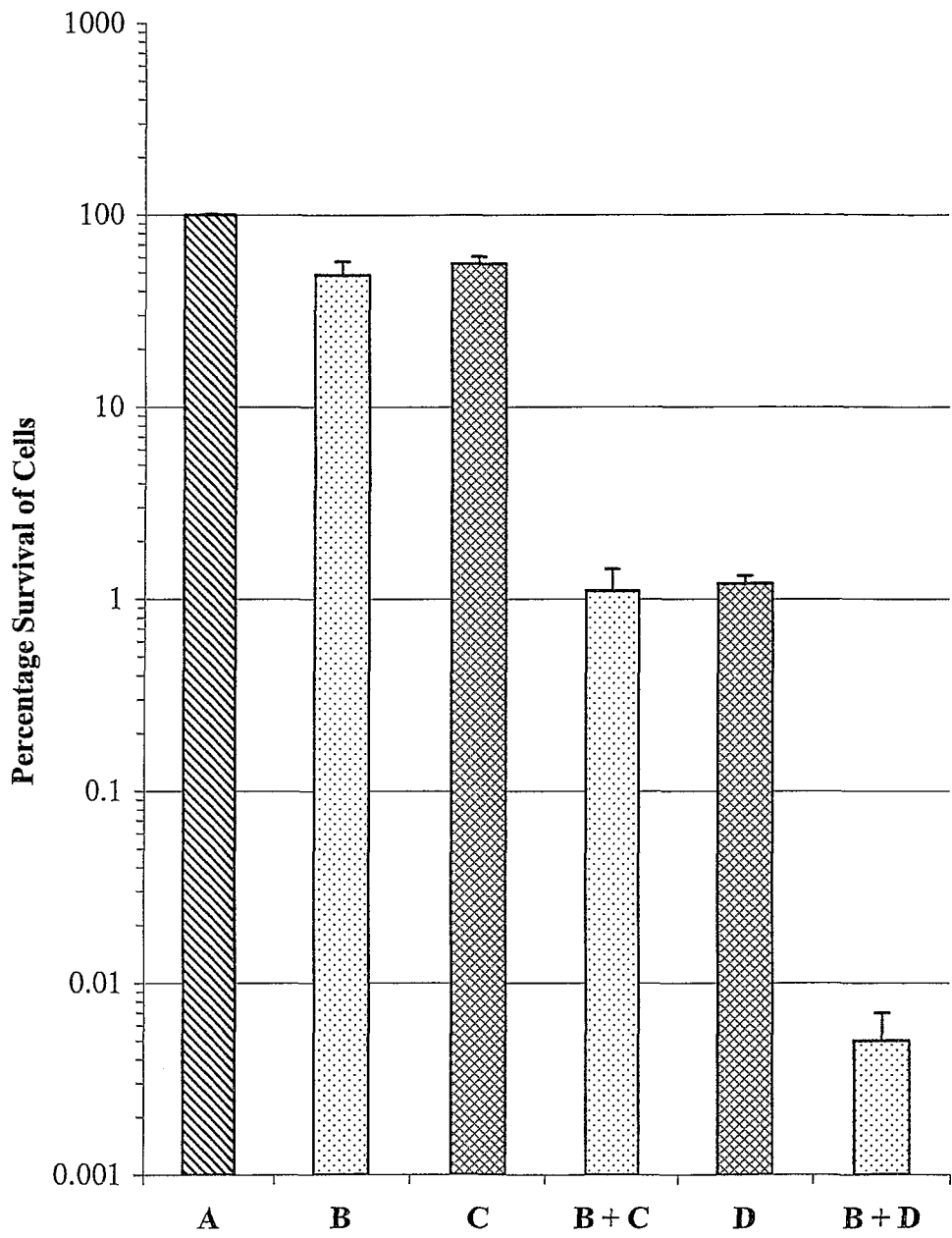

FIG. 7 shows the percentage survival of Chinese Hamster V79 cells over the course of 2 hours at pH 7.5 and 37° C. in a 10 mM phosphate buffer containing 140 mM NaCl and the following:

A: control (i.e. no additional substances);
B: 10 mM DHA;
C: 10 μM E09;
B+C: a combination of 10 mM DHA and 10 μM E09;
D: 100 μM E09; and
B+D: a combination of 10 mM DHA and 100 μM E09.

The survival of V79 cells was determined using the following method:

Volumes (1 mL, $2\times10^5$ cells/mL) of V79 cells in 10 mM phosphate buffer (pH 7.5) containing 140 mM NaCl were incubated at 37° C. and then reagents (as indicated above, at the concentrations stipulated) were added (except for the control experiment). After a 2 hour incubation, the cells were harvested by centrifugation, diluted out serially (4×10-fold) and the cells plated into growth medium and assayed for their colony forming ability after growth for 1 week in a humidified 5% $CO_2$ atmosphere.

As the chart of FIG. 7 demonstrates, the cytotoxic effect of E09 is greatly enhanced by the addition of DHA, which promotes formation of the active form of E09.

In relation to the examples below, tretazicar is commercially available for research purposes from Morvus Technology Limited and Sigma Chemical Company.

EXAMPLE 1

Chemical Activation of Tretazicar

Reported chemical methods of producing the active 4-hydroxylamino derivative from tretazicar use harsh reducing conditions in organic solvents with yields less than 30% (Knox et al, 1993; Knox et al, 1988). I have discovered that dihydroxyacetone (DHA) can reduce tretazicar to the required hydroxylamine in aqueous solution under mildly alkaline conditions. At pH 9 the yield is >85% and the only other product of tretazicar reduction detected is 5-(aziridin-1-yl)-2-hydroxylamino-4-nitrobenzamide.

Figure 1:
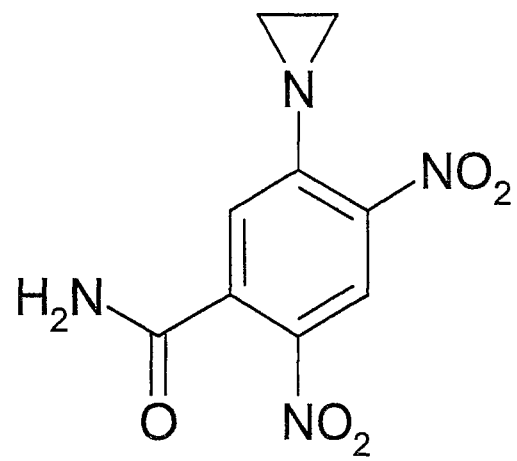
Figure 2:
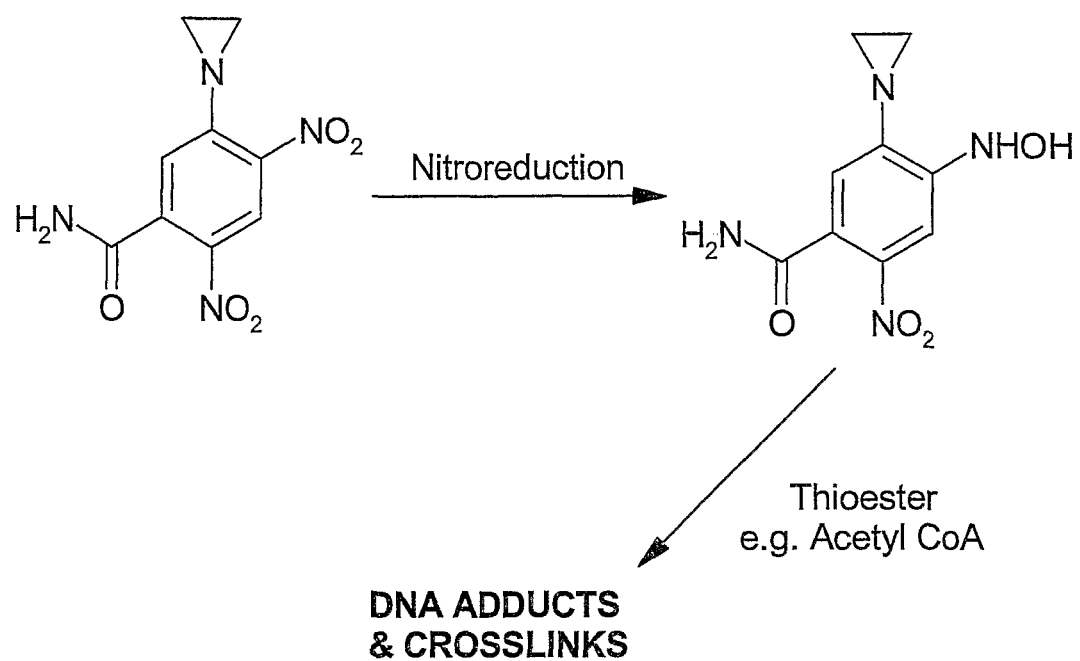
Figure 3:
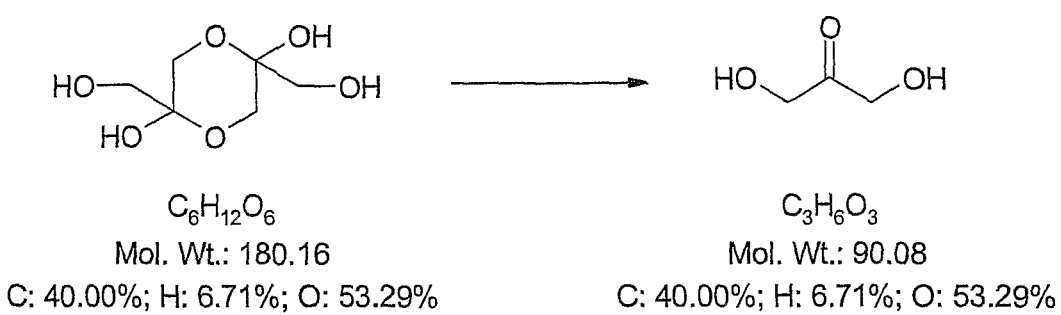

Dihydroxyacetone (DHA; 1,3-dihydroxy-2-propanone; CAS No: 62147-49-3, Beil. 8, 266, Merck Index 13, 3166; FIG. 3) is the active ingredient in sunless or self-tanning lotions and has received approval by the FDA. DHA is a colourless sugar that darkens the skin by staining. It interacts with the dead surface cells found in the epidermis producing a color change. As the dead skin cells are naturally sloughed off, the color gradually fades, typically within 5 to 7 days of application. Sunless tanning products contain dihydroxyacetone concentrations of up to 5%. The higher the concentration, the darker is the tan that will follow. As a tanning agent it stable in pH conditions of between 4 and 6. Too alkali or too acidic results in brown compounds forming, reducing the solutions effectiveness as a tanner. Erythrulose (1,3,4-trihydroxy-2-butanone) is similar in action to DHA, but it does not produce as deep or fast a tan. DHA is produced through the fermentation of glycerine and is a simple three-carbon sugar, non-toxic in nature and comes in the form of a white powder. The normal aim is the dimer ($C_6H_{12}O_6$) but this rapidly reverts to the monomer in solution. The FDA has approved DHA only for external use, and recommends that users should take protective measures to avoid contact with eyes, nose and mucous membranes.

The only adverse effect reported is allergic contact dermatitis. This is reported rarely and most causes of sensitivity in tanning creams are due to other ingredients such as preservatives in the preparation. See the Code of Federal Regulations, page 376:

TITLE 21—FOOD AND DRUGS
CHAPTER I—FOOD AND DRUG ADMINISTRATION, DEPARTMENT OF HEALTH AND HUMAN SERVICES
PART 73—LISTING OF COLOR ADDITIVES EXEMPT FROM CERTIFICATION—Table of Contents
Subpart C—Cosmetics
Sec. 73.2150 Dihydroxyacetone.

DHA has never been reported as a reducing agent. Reducing sugars are known but these are aldoses and have an aldehyde in one end. The aldehyde behaves as a reducing agent and in the presence of mild oxidizing agent, such as $Cu^{2+}$ or $Fe^{3+}$, there is oxidation of the aldehyde to a carboxylic acid. As a ketol an equivalent reaction with DHA is not possible. However, dihydroxyacetone has been shown to promote the formation of hydroxyl radicals in the presence of iron (III) chelates (Malisza & Hasinoff, 1995). This type of reaction may be related to its reducing ability and its alkali instability that results in the formation of brown compounds.

Figure 4:
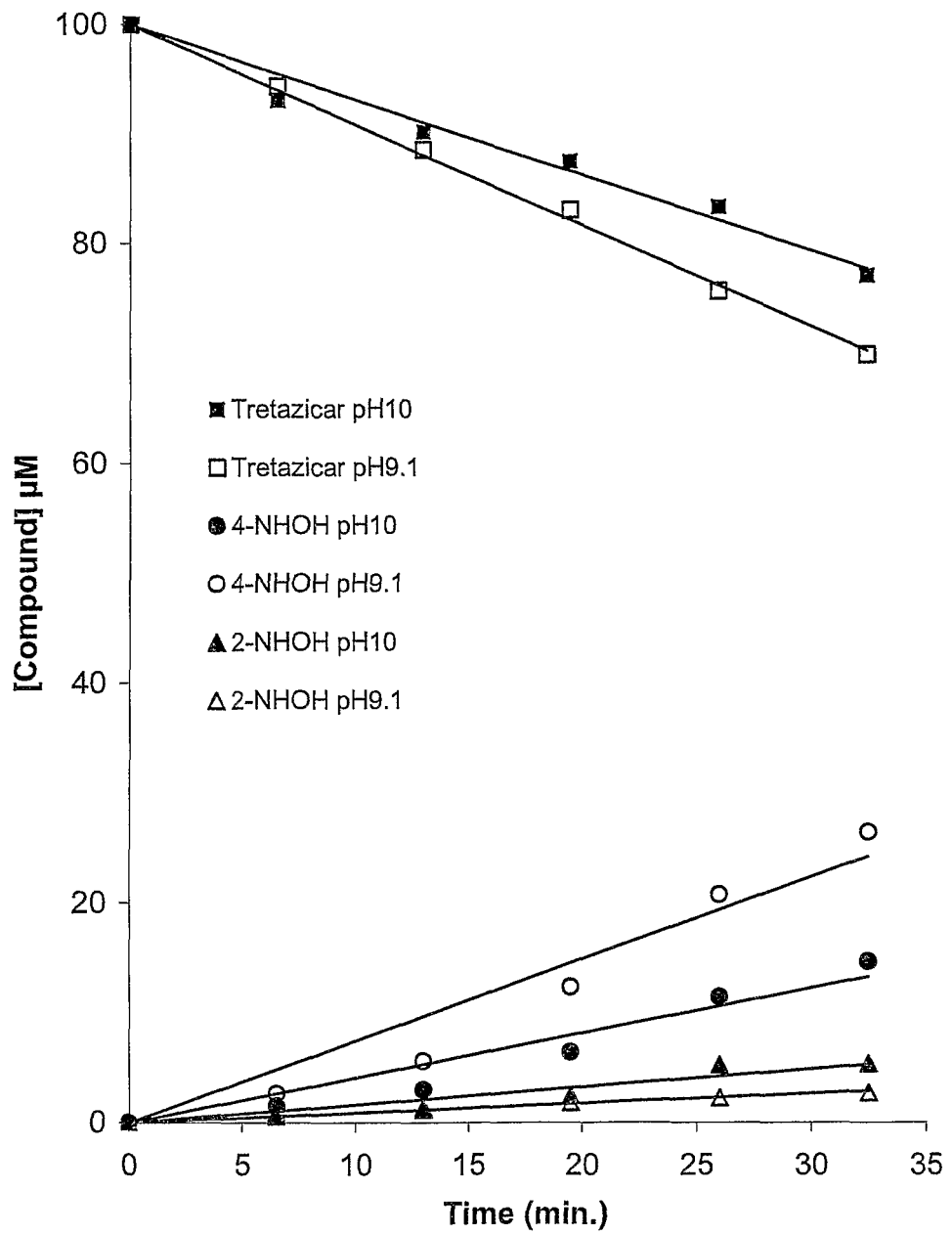
FIG. 4 shows the reduction of tretazicar by DHA.

Under alkali conditions and using an excess of DHA there is a linear rate of reduction of tretazicar with time (FIG. 4).

The assay was started by addition of 100 µL of 100 mM DHA in water to a mixture of tretazicar (100 µM) in 0.1M sodium bicarbonate buffer, pH 9 or pH10, to give a final volume of 1 ml. The mixture was incubated at 37° C. and aliquots (10 µL) were taken every 6 min and assayed immediately by HPLC [Partisil 10 SCX (4.2×150 mm) (Whatinan, Maidstone, Kent, U. K.] eluted isocratically with 0.13 M sodium phosphate (pH 5) at 1.5 mL/min). The concentration of tretazicar was determined in each sample by reference of the corresponding peak area with an external standard, quantified by absorbance at 325 nm. Initial rates were calculated by curve fitting (FigP, Biosoft, Cambridge, U.K.). Reduction products were identified by retention time relative to an authentic standard.

Only two products of tretazicar reduction were observed the 2- and 4-hydroxylamino derivatives. The rate of tretazicar reduction and the proportion of the hydroxylamine products was dependent on pH. Reduction at pH 10 (0.69 nmol/min) was slower than at pH 9 (0.92 nmol/min). After 30 min the ratio of the 4- to the 2-hydroxylamines was 2.7:1 at pH 10 and 9.7:1 at pH 9. Thus, at pH 9, reduction is faster and gives mostly the preferred 4-hydroxylamine product in very high yield (FIG. 4).

DHA or DHA-associated products from the reaction were not detected with the above HPLC method.

EXAMPLE 2

Activation of Tretazicar in a Cream Formulated for Topical Application

Two creams designated A and B have been made. For use, these are mixed in equal amounts. Cream A consists of an E45 base (white soft paraffin BP 14.5% w/w, light liquid paraffin Ph Eur 12.6% w/w, hypoallergenic anhydrous lanolin (Medilan) 1.0% w/w, Crookes Healthcare Ltd, Nottingham, UK) containing 10 mg tretazicar, 10 mg $NaHCO_3$ & 90 mg $Na_2CO_3$ per g. Cream B contains E45 with 100 mg DHA dimer per g. Mixing the two components, A and B, produced a pale yellow cream. This turned brown over a few hours and continued to darken for about 24 hours. Suspension of 200 µg of cream in 1 mL of water with vigorous agitation produced a solution with a pH of about 10 as shown by pH indicating papers. Preliminary experiments with creams containing 10% of the above amounts of buffer salts gave a solution with the same initial pH. However, after 4 hours a solution, prepared as above, was neutral and the cream no longer darkened. This would suggest that by varying the initial buffer concentrations both the duration and extent of the reaction can be controlled.

After mixing and at various times, 200 µg of cream was extracted into 1 mL of DMSO. The extract was then diluted $1/100$ with 50 mM ammonium bicarbonate buffer (pH 10) and analysed by reversed-phase HPLC. At the starting time, analysis of the extract at 325 nm showed only a single major peak and this corresponded to tretazicar as shown by the same retention time and the spectral matching of the UV absorbance spectrum relative to an authentic standard. After 4 hours, analysis of the extract showed many more peaks on both the 260 nm and 325 nm traces (FIG. 5).

Cream A (consisting of an E45 base (white soft paraffin BP 14.5% w/w, light liquid paraffin Ph Eur 12.6% w/w, hypoallergenic anhydrous lanolin (Medilan) 1.0% w/w, Crookes Healthcare Ltd, Nottingham, UK) containing 10 mg tretazicar, 10 mg $NaHCO_3$ & 90 mg $Na_2CO_3$ per g and cream B (containing E45 with 100 mg DHA dimer per g) were mixed and at various times 200 µg was extracted with 1 mL of DMSO with vigorous agitation. The extract was cleared by centrifugation and then diluted $1/100$ with 50 mM ammonium bicarbonate buffer (pH 10) and analysed by HPLC. A sample (10 µL) was injected onto a Waters Symmetry Shield RP18 column (150×3.9 mm) and eluted with a linear gradient (1-40% over 30 minutes) of acetonitrile in 10 mM ammonium formate (pH 4.5). The eluate was continually monitored for UV absorbance between 230 and 400 nm using a TSP UV3000 scanning detector. A.) An extract prepared immediately after the mixing of the cream. B.) An extract from the cream 4 hours after it had been mixed. C.) a synthetic standard of 5-(aziridin-1-yl)-4-hydroxylamino-2-nitrobenzamide. The blue line (the lower line in each pair of traces) is the trace obtained at 260 nm and the red line (the upper line in each pair of traces) the trace obtained at 325 nm. The peak at ~13 minutes is CB 1954 and the large 260 nm peak at ~19 minutes comes from the E45. It is not possible to measure the efficiency of the extraction method.

Tretazicar was still detected and a peak with a retention time of ~5.0 minutes was identified as the 4-hydroxylamine of tretazicar as indicated by the same retention time and the spectral matching of the UV absorbance spectrum relative to an authentic standard (FIG. 6). The other peaks did not correspond to known tretazicar reduction products and may have arisen from the oxidation of DHA or reaction of reduced tretazicar products with either cream or DHA.

The active form of tretazicar, (5-(aziridin-1-yl)-4-hydroxylamino-2-nitrobenzamide), is formed in the E45 based cream.

EXAMPLE 3

Topical Application of a Tretazicar Cream

A cream formulated above was mixed and about 0.1 g applied to a wart (growing, dome 1.5 mm high) located on the finger of a healthy human volunteer and covered with a plaster. An initial warmth was reported from the applied cream. After about 4 hours the plaster was removed and the wart was found to have sloughed off and left a pit of ~1 mm depth. The immediate surrounding tissue had a yellow colouration. This gradually turned white over a few days and no re-growth of the wart was reported after 6 weeks. No adverse affects were apparent or reported.

Cream A (consisting of an E45 base (white soft paraffin by 14.5% w/w, light liquid paraffin Ph Eur 12.6% w/w, hypoallergenic anhydrous lanolin (Medilan) 1.0% w/w, Crookes Healthcare Ltd, Nottingham, UK) containing 10 mg tretazicar, 10 mg $NaHCO_3$ & 90 mg $Na_2CO_3$ per g and cream B (containing E45 with 100 mg DHA dimer per g) were mixed and applied (100 µg) to a wart (growing, dome 1.5 mm high) located on the finger of a healthy human volunteer and covered with a plaster. After about 4 hours the plaster was removed and the wart was found to have sloughed off and left a pit of ~1 mm depth. The immediate surrounding tissue had a yellow colouration. This gradually turned white over a few days and no re-growth of the wart was reported after 6 weeks. No adverse affects were apparent or reported. The photograph was taken after 1 week.

Activation of tretazicar in a topical application has a marked effect on a wart with minimal effects on normal surrounding tissue.

EXAMPLE 4

Treatment of Bladder Cancer

Bladder chemotherapy instillations, or intravesical chemotherapy, are given to people who have superficial bladder cancer by filling the bladder with medication to fight the cancer cells. Although superficial bladder cancers are an early form of cancer, many will recur after initial removal. However, by using treatment which puts medication directly in contact with the bladder wall, it may well be possible to prevent recurrence or lengthen the time until recurrence. Intravesical chemotherapy is a brief procedure. A catheter is put into the bladder through the urethra. Tretazicar in bicarbonate buffer (pH 9) is instilled over 2 to 3 minutes, followed by an infusion, of DHA in water over a similar time. The catheter is removed and after 2 hours the medication removed by urination.

EXAMPLE 5

DHA Reduction of Prodrugs at Near Neutral pH

Assay: HPLC

The assay mixture contained the compound under test (100 µM) and DHA (10 mM) in a final reaction volume of 1 mL of sodium phosphate buffer (of the required pH). The reaction was started by addition of DHA and the mixture is incubated at 37° C. Aliquots (10 µL) were taken every 20 min and assayed immediately by HPLC on a Partisphere 5 C18 (4.2× 150 mm) column (Whatman, Maidstone, Kent, U.K.], eluted with a gradient of acetonitrile in water (1-95% over 10 minutes) at 2.0 mL per minute. The eluate was continuously monitored for absorbance using a photodiode array UV-VIS detector. The concentration of drug was determined in each sample by reference of the corresponding peak area with an external standard and quantified by absorbance at a suitable wavelength determined from the PDA scan. Initial rates were calculated by curve fitting (FigP software).

|              |           | INITIAL RATE (nmoles/min/mL) | |
| Compound | Structure | 0.1 M PO$_4$, pH7.5 | 0.1 M PO$_4$, pH8 |
| --- | --- | --- | --- |
| Tretazicar | 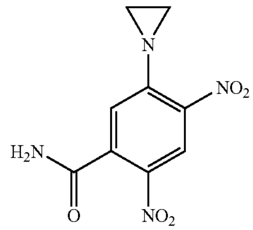 [SMILES: NC(=O)c1cc(N2CC2)c([N+](=O)[O-])cc1[N+](=O)[O-]] | <0.01 | 0.158 |
| Metronidazole | 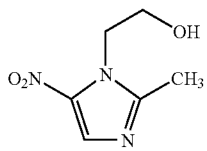 | 0.131 | 0.369 |
| Misonidazole | 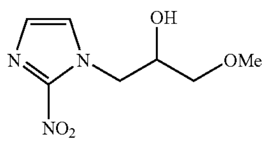 [SMILES: COCC(O)Cn1ccnc1[N+](=O)[O-]] | 0.221 | 1.922 |
| Nitrofurazone | 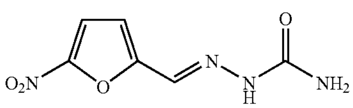 [SMILES: NC(=O)N/N=C/c1ccc([N+](=O)[O-])o1] | 0.177 | 0.203 |
| RSU-1069/ RB-1645 | 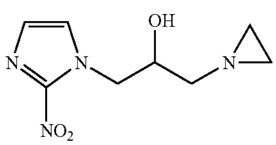 [SMILES: O=[N+]([O-])c1nccn1CC(O)CN1CC1] | <0.01 | 2.57 |
| Tirapazamine | 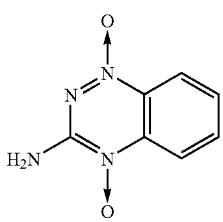 [SMILES: Nc1n[n+]([O-])c2ccccc2[n+]1[O-]] | 0.523 | 0.512 |
| Mitomycin C | 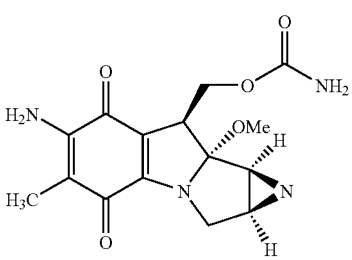 [SMILES: CO[C@@]12[C@H](COC(N)=O)C3=C(C(=O)C(C)=C(N)C3=O)N1C[C@@H]1N[C@@H]12] | 1.524 (PBS) | 0.052[a] |
| E09 | 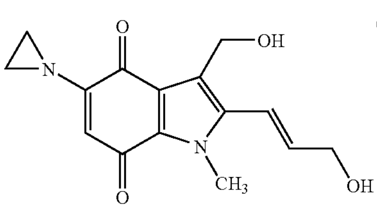 [SMILES: Cn1c(/C=C/CO)c(CO)c2c1C(=O)C=C(N1CC1)C2=O] | 0.272 | 0.605 |

Notes
[a] 1 mM DHA employed (instead of 10 mM DHA)

EXAMPLE 6

DHA Reduction of Nitro Compounds and Prodrugs at Various pH Values

Samples were assayed as described above for Example 5.

| Name | Structure | pH | Initial Rate (nmoles/min/mL) |
|---|---|---|---|
| Tretazicar | 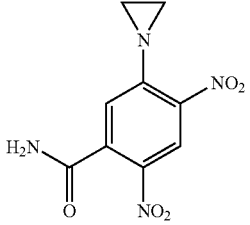 | 8<br>9<br>10<br>10.6 | 0.158<br>0.933<br>1.248<br>5.801 |
| 5-chloro-2,4-dinitrotoluene | 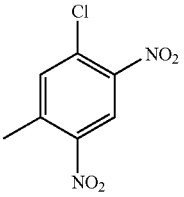 | 8<br>9<br>10<br>10.6 | 0.132<br>0.499<br>0.690<br>1.703 |
| 4-nitrobenzyl alcohol | 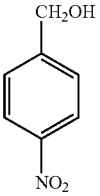 | 8<br>9<br>10<br>10.6 | <0.01<br><0.01<br>0.105<br>0.087 |
| 4-chloro-3,5-dinitrobenzoic acid | 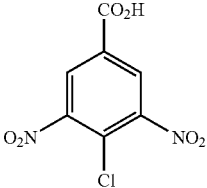 [SMILES: O=C(O)c1cc([N+](=O)[O-])c(Cl)c([N+](=O)[O-])c1] | 8<br>9<br>10<br>10.6 | 0.195<br>1.293<br>1.727<br>2.442 |
| Misonidazole | 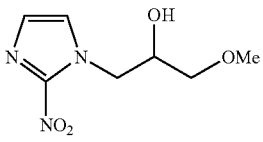 | 8<br>9<br>10<br>10.6 | 1.922<br>1.851<br>3.180<br>— |
| Metronidazole | 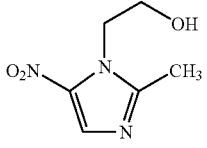 | 8<br>9<br>10<br>10.6 | 0.369<br>0.890<br>1.239<br>0.087 |
| Mitomycin C | 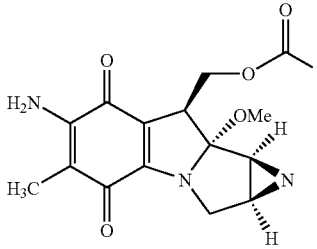 | 7<br>8<br>8.5<br>9 | 1.019<br>0.052[a]<br>0.103[a]<br>Too fast to measure |

-continued

| Name | Structure | pH | Initial Rate (nmoles/min/mL) |
|---|---|---|---|
| Nitrofurazone | 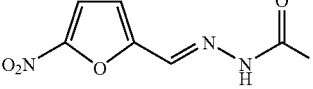 | 7.5<br>8<br>8.5<br>9<br>10 | 0.177<br>0.203<br>0.260<br>2.390<br>3.789 |
| Tirapazamine | 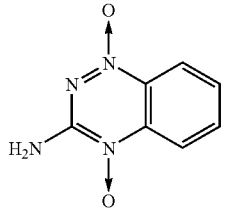 | 7.5<br>8<br>8.5<br>9<br>10 | 0.523<br>0.512<br>0.639<br>3.503<br>4.209 |

Notes
[a] 1 mM DHA employed (instead of 10 mM DHA)

EXAMPLE 7

Reduction of NADP⁺ by α-Hydroxycarbonyl Compounds

A 10 μL aliquot of test compound (at a concentration of 100 mM in water) is added to a 200 μM NADP⁺ aqueous solution (approximately 990 μL), buffered to pH 10 (1 mM NaHCO₃ buffer). The final concentration of the test compound in the assay solution was 1 mM. Reduction of NADP⁺ was then monitored by measuring the increase, over the course of 2 minutes, of absorption at 350 nM on a spectrophotometer. Initial rates were recorded as the change in A350 per minute.

| Compound | Structure | Rate |
|---|---|---|
| Dihydroxyacetone (dimer)[1] | 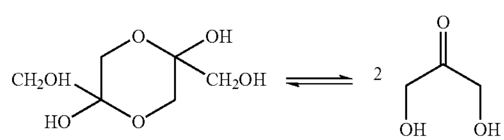 [SMILES: OCC1(O)COC(O)(CO)CO1 ; O=C(CO)CO] | 0.063 |
| Hydroxyacetone (acetol)[2] | 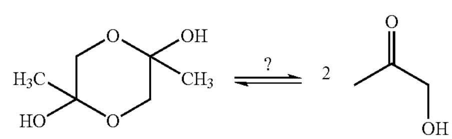 | 0.003 |
| D,L-Glyceraldehyde[3] | 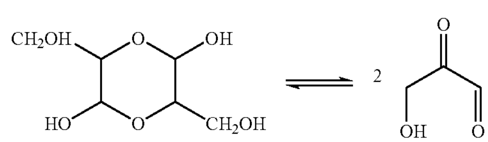 [SMILES: OCC1OC(O)C(CO)OC1O ; O=CC(=O)CO] | 0.015 |
| Glycolaldehyde dimer[4] | 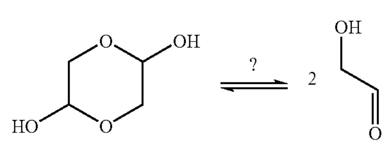 | 0.029 |
| D(-)-Erthrose[5] | 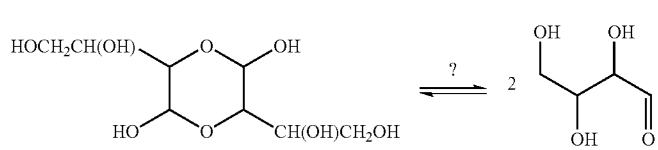 | 0.004 |

-continued

| Compound | Structure | Rate |
|---|---|---|
| L-Xylulose | HOCH₂CH(OH), CH₂OH, HO, O, OH, CH₂OH, CH(OH)CH₂OH ⇌ 2 OH O OH OH OH | 0.003 |

Notes
1. Supposed to form monomer in solution.
2. Technical grade (>90%) used. Lag of about 60 s before any increase in absorption at 350 nm observed.
3. Concentration calculated for monomer.
4. Mix of stereoisomers. No effect on rate observed after addition of 1 mM EDTA to the reaction mixture.
5. Only ~50% pure. Lag of about 90 s before any increase in absorption at 350 nm observed.

Without wishing to be bound by theory, it is believed that the compounds showing reducing activity in the above assay are a-hydroxycarbonyl compounds that are capable of forming cyclic dimers of the type depicted in Formula Ia.

In contrast, compounds for which rate in the above assay determined to be below 0.001 (i.e. for which no reducing activity detected) include the following:
glycerol;
glyoxal;
D-glucose;
diglycolic anhydride;
(±)-tetrahydrofurfuryl alcohol;
1,4-dioxane-2,3-diol; and
2-(hydroxymethyl)tetrahydropyran.

EXAMPLE 8

Reduction of Tretazicar by α-Hydroxycarbonyl Compounds

The assay was started by addition of 100 µL of 100 mM test compound (compound of formula I) in water to a mixture of tretazicar (100 µM) in 0.1 M sodium bicarbonate buffer, pH 9 or pH 10, to give a final volume of 1 mL. The mixture was incubated at 37° C. and aliquots (10 µL) were taken every 6 min and assayed immediately by HPLC [Partisil 10 SCX (4.2×150 mm) (Whatman, Maidstone, Kent, U.K.] eluted isocratically with 0.13 M sodium phosphate (pH 5) at 1.5 mL/min). The concentration of tretazicar was determined in each sample by reference of the corresponding peak area with an external standard, quantified by absorbance at 325 nm. Initial rates were calculated by curve fitting (FigP, Biosoft, Cambridge, U.K.). Reduction products were identified by retention time relative to an authentic standard.

| Compound | Structure | pH | Initial Rate (nmoles/min/mL) |
|---|---|---|---|
| Dihydroxyacetone (used in dimeric form) | HO O OH | 9 10 | 0.92 0.69 |
| D,L-Glyceraldehyde[3] | OH HO O | 9 10 | 0.53 0.62 |
| Glycolaldehyde (used in dimeric form)[4] | OH O | 9 10 | 0.18 0.14 |
| D(−)-Erthrose[5] | OH OH OH O | 9 10 | <0.01 0.28 |
| L-Xylulose | OH O OH OH OH | 9 10 | <0.01 0.28 |
| 3-hydroxy-2-butanone | O OH | 9 10 | 0.034 0.184 |

In contrast, compounds for which rate in the above assay determined to be below 0,001 (i.e. for which no reducing activity detected) include the following:
glycerol;
glyoxal;
D-glucose;
diglycolic anhydride;
(±)-tetrahydrofurfuryl alcohol;
2-(hydroxymethyl)tetrahydropyran;
4-hydroxy-2-butanone;
dichloroacetone;
1,4-dioxane-2,3-diol; and
dichloroacetyl chloride.

EXAMPLE 9

Large-Scale Reduction of Tretazicar to the Corresponding Hydroxylamine

A solution of 5-(aziridin-1-yl)-2,4-dinitrobenzamide ("CB 1954", 1.00 g, 3.97 mmol) in methanol ('AnalaR'-grade, 40 mL) was treated with excess powdered anhydrous $K_2CO_3$ (10.0 g, 72 mmol; aprox. 18 equiv.) and the mixture was heated to 60° C. with stirring. The suspension was stirred at 60° C. beneath a $N_2$ blanket stream atmosphere. A solution of 1,3-dihydroxyacetone (1.50 g as DHA dimer, 8.33 mmol; 2.1 mol equiv) in methanol ('AnalaR'-grade, 40 mL), previously deaerated by flushing with $N_2$ gas, was then added during 15 min to the reaction mixture with rapid stirring while maintaining the temperature at 60° C. A fast reaction is observed with a colour change from pale yellow-orange to brown. Thin-layer chromatography (TLC; Merck silica gel 60 GF254 on aluminium sheets, 9:1 v/v $CH_2Cl_2$ : MeOH) showed quantitative removal of the CB 1954 starting material (Rf 0.73) and formation of two polar products at Rf 0.53 and Rf 0.47. The two products showed identical TLC behaviour to authentic 5-(aziridin-1-yl)-2-hydroxylamino-4-nitrobenzamide and 5-(aziridin-1-yl)-4-hydroxylamino-2-nitrobenzamide samples, respectively, prepared by published methods [Knox, R. J., Friedlos, F., Jarman, M., Roberts, J. J. *Biochemical Pharmacology* 37, 4661-4669 (1988); Knox, R. J., Friedlos, F., Biggs, P. J., Flitter, W. D. Gaskell, M., Goddard, P., Davies, L., Jarman, M. *Biochemical Pharmacology* 46, 797-803 (1993)].

The reaction mixture was filtered while hot and the insoluble material was washed with cold methanol (10 mL). The combined filtrate was cooled and rotary evaporated (30° C., high-vacuum) to give a viscous yellow-brown oil (1.02 g, >100%). TLC examination confirmed that two major products were present. Minor spots (<1-2% total, Rf 0.62, 0.66) corresponding to the 2-nitroso and 4-nitroso oxidation products resulting from O2 oxidation under alkaline conditions during handling and work-up were also evident. (Note: exposure to air should be minimised by flushing all apparatus with $N_2$ gas to prevent oxidation of the hydroxylamines to nitroso products and unwanted coloured by-products). The 2-hydroxylamine (Rf 0.53) and 4-hydroxylamine (Rf 0.47) reaction products were judged to be formed in ~40:60 ratio. Chromatographic separation of the isomers is hampered by their close elution properties using available solvent systems. However, flash chromatographic separation of a crude mixture sample (100 mg) (Merck silica gel, 60-200 mesh, 9:1 v/v $CH_2Cl_2$—MeOH) gave 5-(aziridin-1-yl)-2-hydroxylamino-4-nitrobenzamide (31 mg) and 5-(aziridin-1-yl)-4-hydroxylamino-2-nitrobenzamide (49 mg) after solvent removal from fractions. Both products gave NMR spectra consistent with the reported properties for the isomeric hydroxylamines and TLC behaviour that was indistinguishable with the authentic compounds [Knox, R. J., Friedlos, F., Jarman, M., Roberts, J. J. *Biochemical Pharmacology* 37, 4661-4669 (1988)].

Notes:
(1) The preferred reaction solvent is methanol. 1,3-Dihydroxyacetone (DHA) dimer has limited solubility in many common solvents, including acetone and higher alcohols.
(2) Reaction is almost instantaneous at 60° C. but is slower at lower temperatures. The use of higher temperature reaction systems may have an adverse effect on relative product yield.

The product hydroxylamines show greater sensitivity to air oxidation in the presence of alkali, hence it is recommended that the $K_2CO_3$ reagent is removed from the reaction mixture as soon as possible. Chromatographic separation of the mixture containing the 2- and 4-hydroxylamine products requires minimisation of any exposure for dissolved material to $O_2$ (air) during handling.

References

Anlezark, G. M., Melton, R. G., Sherwood, R. F., Coles, B., Friedlos, F. & Knox, R. J. (1992). The bioactivation of 5-(aziridin-1-yl)-2,4-dinitrobenzamide (CB1954)-I. Purification and properties of a nitroreductase enzyme from *Escherichia coli*—a potential enzyme for antibody-directed enzyme prodrug therapy (ADEPT). *Biochem Pharmacol*, 44, 2289-95.

Anlezark, G. M., Melton, R. G., Sherwood, R. F., Wilson, W. R., Denny, W. A., Palmer, B. D., Knox, R. J., Friedlos, F. & Williams, A. (1995). Bioactivation of dinitrobenzamide mustards by an *E. coli* B nitroreductase. *Biochem Pharmacol*, 50, 609-18.

Bailey, S. M., Knox, R. J., Hobbs, S. M., Jenkins, T. C., Mauger, A. B., Melton, R. G., Burke, P. J., Connors, T. A. & Hart, I. R. (1996). Investigation of alternative prodrugs for use with *E. coli* nitroreductase in 'suicide gene' approaches to cancer therapy. *Gene Ther*, 3, 1143-50.

Boland, M. P., Knox, R. J. & Roberts, J. J. (1991). The differences in kinetics of rat and human DT diaphorase result in a differential sensitivity of derived cell lines to CB 1954 (5-(aziridin-1-yl)-2,4-dinitrobenzamide). *Biochem Pharmacol*, 41, 867-75.

Bridgewater, J. A., Knox, R. J., Pitts, J. D., Collins, M. K. & Springer, C. J. (1997). The bystander effect of the nitroreductase/CB1954 enzyme/prodrug system is due to a cell-permeable metabolite. *Hum Gene Ther*, 8, 709-17.

Bridgewater, J. A., Springer, C. J., Knox, R. J., Minton, N. P., Michael, N. P. & Collins, M. K. (1995). Expression of the bacterial nitroreductase enzyme in mammalian cells renders them selectively sensitive to killing by the prodrug CB1954. *Eur J Cancer*, 31a, 2362-70.

Burke, P. J. & Knox, R. J. (1998). Therapeutic systems PCT/GB98/01731); WO 98/57662.

Chung-Faye, G., Palmer, D., Anderson, D., Clark, J., Downes, M., Baddeley, J., Hussain, S., Murray, P. I., Searle, P., Seymour, L., Harris, P. A., Ferry, D. & Kerr, D. J. (2001). Virus-directed, enzyme prodrug therapy with nitroimidazole reductase: a phase I and pharmacokinetic study of its prodrug, CB1954. *Clin Cancer Res*, 7, 2662-8.

Cobb, L. M. (1970). Toxicity of the selective antitumor agent 5-aziridino-2,4-dinitrobenzamide in the rat. *Toxicol Appl Pharmacol*, 17, 231-238.

Connors, T.A. & Melzack, D. H. (1971). Studies on the mechanism of action of 5-aziridinyl-2,4-dinitrobenzamide (CB 1954), a selective inhibitor of the Walker tumour. *Int J Cancer*, 7, 86-92.

Cui, W., Allen, N. D., Skynner, M., Gusterson, B. & Clark, A. J. (2001). Inducible ablation of astrocytes shows that these cells are required for neuronal survival in the adult brain. *Glia*, 34, 272-82.

Cui, W., Gusterson, B. & Clark, A. J. (1999). Nitroreductase-mediated cell ablation is very rapid and mediated by a p53-independent apoptotic pathway. *Gene Ther*, 6, 764-70.

Felmer, R., Cui, W. & Clark, A. J. (2002). Inducible ablation of adipocytes in adult transgenic mice expressing the *e. Coli* nitroreductase gene. *J Endocrinol*, 175, 487-98.

Friedlos, F., Court, S., Ford, M., Denny, W. A. & Springer, C. (1998). Gene-directed enzyme prodrug therapy—quantitative bystander cytotoxicity and DNA damage induced by CB 1954 in cells expressing bacterial nitroreductase. *Gene Therapy*, 5, 105-112.

Friedlos, F., Quinn, J., Knox, R. J. & Roberts, J. S. (1992). The properties of total adducts and interstrand crosslinks in the DNA of cells treated with CB 1954. Exceptional frequency and stability of the crosslink. *Biochem Pharmacol*, 43, 1249-54.

Hu, L., Yu, C., Jiang, Y., Han, J., Li, Z., Browne, P., Race, P. R., Knox, R. J., Searle, P. F. & Hyde, E. I. (2003). Nitroaryl phosphoramides as novel prodrugs for *E. coli* nitroreductase activation in enzyme prodrug therapy. *J Med Chem*, 46, 4818-21.

Isles, A. R., Ma, D., Milsom, C., Skynner, M. J., Cui, W., Clark, J., Keveme, E. B. & Allen, N. D. (2001). Conditional ablation of neurones in transgenic mice. *J Neurobiol*, 47, 183-93.

Knox, R. J., Burke, P. J., Chen, S. & Kerr, D. J. (2003). CB 1954: from the Walker tumor to NQO2 and VDEPT. *Curr Pharm Des*, 9, 2091-104.

Knox, R. J., Friedlos, F., Biggs, P. J., Flitter, W. D., Gaskell, M., Goddard, P., Davies, L. & Jarman, M. (1993). Identification, synthesis and properties of 5-(aziridin-1-yl)-2-nitro-4-nitrosobenzamide, a novel DNA crosslinking agent derived from CB1954. *Biochem Pharmacol*, 46, 797-803.

Knox, R. J., Friedlos, F., Jarman, M. & Roberts, J. J. (1988). A new cytotoxic, DNA interstrand crosslinking agent, 5-(aziridin-1-yl)-4-hydroxylamino-2-nitrobenzamide, is formed from 5-(aziridin-1-yl)-2,4-dinitrobenzamide (CB 1954) by a nitroreductase enzyme in Walker carcinoma cells. *Biochem Pharmacol*, 37, 4661-9.

Knox, R. J., Friedlos, F., Lydall, D. A. & Roberts, J. J. (1986). Mechanism of cytotoxicity of anticancer platinum drugs: evidence that cis-diamminedichloroplatinum(II) and cis-diammine-(1,1-cyclobutanedicarboxylato)platinum(II) differ only in the kinetics of their interaction with DNA. *Cancer Res*, 46, 1972-9.

Knox, R. J., Friedlos, F., Marchbank, T. & Roberts, J. J. (1991a). Bioactivation of CB 1954: reaction of the active 4-hydroxylamino derivative with thioesters to form the ultimate DNA-DNA interstrand crosslinking species. *Biochem Pharmacol*, 42, 1691-7.

Knox, R. J., Friedlos, F., Sherwood, R. F., Melton, R. G. & Anlezark, G. M. (1992). The bioactivation of 5-(aziridin-1-yl)-2,4-dinitrobenzamide (CB1954)-II. A comparison of an *Escherichia coli* nitroreductase and Walker D T diaphorase. *Biochem Pharmacol*, 44, 2297-301.

Knox, R. J., Jenkins, T. C., Hobbs, S. M., Chen, S., Melton, R. G. & Burke, P. J. (2000). Bioactivation of 5-(aziridin-1-yl)-2,4-dinitrobenzamide (CB 1954) by human NAD(P)H quinone oxidoreductase 2: a novel co-substrate-mediated antitumor prodrug therapy. *Cancer Res*, 60, 4179-86.

Knox, R. J., Lydall, D. A., Friedlos, F., Basham, C., Rawlings, C. J. & Roberts, J. J. (1991b). The Walker 256 carcinoma: a cell type inherently sensitive only to those difunctional agents that can form DNA interstrand crosslinks. *Mutat Res*, 255, 227-40.

Knox, R. J., Lydall, D. A., Friedlos, F., Basham, C. & Roberts, J. J. (1987). The effect of monofunctional or difunctional platinum adducts and of various other associated DNA damage on the expression of transfected DNA in mammalian cell lines sensitive or resistant to difunctional agents. *Biochim Biophys Acta*, 908, 214-23.

Li, Z., Han, J., Jiang, Y., Browne, P., Knox, R. J. & Hu, L. (2003). Nitrobenzocyclophosphamides as potential prodrugs for bioreductive activation: synthesis, stability, enzymatic reduction, and antiproliferative activity in cell culture. *Bioorg Med Chem*, 11, 4171-8.

Ma, D., Allen, N. D., Van Bergen, Y. C., Jones, C. M., Baum, M. J., Keveme, E. B. & Brennan, P. A. (2002). Selective ablation of olfactory receptor neurons without functional impairment of vomeronasal receptor neurons in OMP-ntr transgenic mice. *Eur J Neurosci*, 16, 2317-23.

Malisza, K. L. & Hasinoff, B. B. (1995). Doxorubicin reduces the iron(III) complexes of the hydrolysis products of the antioxidant cardioprotective agent dexrazoxane (ICRF-187) and produces hydroxyl radicals. *Arch Biochem Biophys*, 316, 680-8.

Mauger, A. B., Burke, P. J., Somani, H. H., Friedlos, F. & Knox, R. J. (1994). Self-immolative prodrugs: candidates for antibody-directed enzyme prodrug therapy in conjunction with a nitroreductase enzyme. *J Med Chem*, 37, 3452-8.

Sheard, C. E., Double, J. A. & Berenbaum, M. C. (1971). The sensitivity to chemopherapeutic agents of a rat tumour grown in immunosuppressed mice. *Br J Cancer*, 25, 838-844.

Workman, P., Morgan, J. E., Talbot, K., Wright, K. A., Donaldson, J. & Twentyman, P. R. (1986a). CB 1954 revisited. II. Toxicity and antitumour activity. *Cancer Chemother Pharmacol*, 16, 9-14.

Workman, P., White, R. A. & Talbot, K. (1986b). CB 1954 revisited. I. Disposition kinetics and metabolism. *Cancer Chemother Pharmacol*, 16, 1-8.

Wu, K., Knox, R., Sun, X. Z., Joseph, P., Jaiswal, A. K., Zhang, D., Deng, P. S. & Chen, S. (1997). Catalytic properties of NAD(P)H:quinone oxidoreductase-2 (NQO2), a dihydronicotinamide riboside dependent oxidoreductase. *Arch Biochem Biophys*, 347, 221-8.

All references mentioned herein are incorporated herein by reference.

The invention claimed is:

1. A method of reducing a reduction-activated prodrug, the method comprising contacting the reduction-activated prodrug with a compound of formula I, or a dimer thereof, wherein the reduction-activated prodrug is tretazicar (5-(aziridin-1-yl)-2,4-dinitrobenzamide), and wherein the reduction-activated prodrug tretazicar (5-(aziridin-1-yl)-2,4-dinitrobenzamide) is reduced to give more 5-(aziridin-1-yl)-4-hydroxylamino-2-nitrobenzamide than 5-(aziridin-1-yl)-2-hydroxylamino-4-nitrobenzamide, and wherein the compound of formula I has the structure:

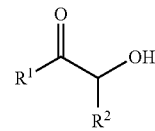

wherein $R^1$ is —H, aryl, Het, or $C_{1-12}$ alkyl, wherein the $C_{1-12}$ alkyl is optionally substituted by one or more substituents selected from —OH, halo, and $C_{1-3}$ alkoxy;

wherein $R^2$ is —H or $C_{1-6}$ alkyl, wherein the $C_{1-6}$ alkyl is optionally substituted by one or more —OH groups;

wherein aryl is a $C_{6-10}$ carbocyclic aromatic group optionally substituted by one or more substituents selected from halo, $C_{1-6}$ alkyl, and $C_{1-6}$ alkoxy;

wherein Het is a 4- to 14-membered heterocyclic group comprising one, two, or three rings, and comprising one or more heteroatoms independently selected from oxygen, nitrogen, and sulfur, wherein the heterocyclic group is optionally substituted by one or more substituents selected from halo, $C_{1-6}$ alkyl, and $C_{1-6}$ alkoxy; and wherein the compound of formula I is capable of forming a cyclic dimer of formula Ia:

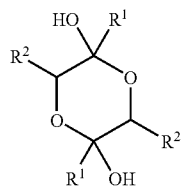

wherein $R^1$ and $R^2$ are as defined above; and wherein the reduction is carried out at a temperature from ambient to 70° C.; and:

(a) is effected at a pH of between 7 and 10.4; and (b) is conducted in the presence of a base that is a carbonate salt or a bicarbonate salt.

2. The method of claim 1, wherein the compound of formula I is dihydroxyacetone (DHA), erythrulose, or a dimer thereof.

3. The method of claim 1, wherein the method comprises:

(a) providing a mixture of tretazicar (5-(aziridin-1-yl)-2,4-dinitrobenzamide) and a base that is a carbonate salt or a bicarbonate salt; and (b) adding a compound of formula I, or a dimer thereof.

4. The method of claim 3, wherein the compound of formula I is dihydroxyacetone (DHA), erythrulose, or a dimer thereof.

5. The method of claim 3, wherein the reduction-activated prodrug is converted to 5-(aziridin-1-yl)-4-hydroxylamino-2-nitrobenzamide and 5-(aziridin-1-yl)-2-hydroxylamino-4-nitrobenzamide, and wherein the method further comprises the step of separating 5-(aziridin-1-yl)-4-hydroxylamino-2-nitrobenzamide from 5-(aziridin-1-yl)-2-hydroxylamino-4-nitrobenzamide.

6. The method of claim 1, wherein reduction of the reduction-activated prodrug is performed in a solvent system comprising at most 5% by weight of water.

7. The method of claim 6, wherein reduction of the reduction-activated prodrug is performed in a solvent system comprising at most 1% by weight of water.

8. A method of reducing a reduction-activated prodrug, the method comprising contacting the reduction-activated prodrug with a compound of formula I, or a dimer thereof, wherein the reduction-activate prodrug is tretazicar (5-(aziridin-1-yl)-2,4-dinitrobenzamide), and wherein the compound of formula I is dihydroxyacetone (DHA), glycolaldehyde, glyceraldehyde, erythrose, xylulose, erythrulose, 3-hydroxy-2-butanone, or a dimer thereof; and wherein the reduction is carried out at a temperature from ambient to 70° C.; and (a) is effected at a pH of between 7 and 10.4; or (b) is conducted in the presence of a base that is an amine, a nitrogen-based heterocycle, a carbonate salt or a bicarbonate salt.

9. A method of reducing a reduction-activated prodrug, the method comprising contacting the reduction-activated prodrug with a compound of formula I, or a dimer thereof, wherein the reduction-activate prodrug is tretazicar (5-(aziridin-1-yl)-2,4-dinitrobenzamide), and wherein the compound of formula I is dihydroxyacetone (DHA), glycolaldehyde, glyceraldehyde, erythrose, xylulose, erythrulose, 3-hydroxy-2-butanone, or a dimer thereof; and wherein the reduction is carried out at a temperature from ambient to 70° C.; and (a) is effected at a pH of between 7 and 10.4; and (b) is conducted in the presence of a base that is a carbonate salt or a bicarbonate salt.

10. A method of reducing a reduction-activated prodrug, the method comprising contacting the reduction-activated prodrug with a compound of formula I, or a dimer thereof, wherein the reduction-activate prodrug is tretazicar (5-(aziridin-1-yl)-2,4-dinitrobenzamide), and wherein the reduction-activated prodrug tretazicar (5-(aziridin-1-yl)-2,4-dinitrobenzamide) is reduced to give more 5-(aziridin-1-yl)-4-hydroxylamino-2-nitrobenzamide) than 5-(aziridin-1-yl)-2-hydroxylamino-4-nitrobenzamide), and wherein the compound of formula I is dihydroxyacetone (DHA), glycolaldehyde, glyeraldehyde, erythrose, xylulose, erythrulose, 3-hydroxy-2-butanone, or a dimer thereof; and wherein the reduction is carried out at a temperature from ambient to 70° C.; and (a) is effected at a pH of between 7 and 10.4; and (b) is conducted in the presence of a base that is a carbonate salt or a bicarbonate salt.

* * * * *